United States Patent
Sandoval et al.

(10) Patent No.: US 11,998,628 B2
(45) Date of Patent: Jun. 4, 2024

(54) PERSONAL CARE COMPOSITIONS

(71) Applicant: Colgate-Palmolive Company, New York, NY (US)

(72) Inventors: Federico Daniel Sandoval, Mexico City (MX); Arturo Zuniga, Mexico City (MX); Simon Elias, Mexico City (MX); Karina Camacho, Mexico City (MX); Alp Uray, Mountainside, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/977,139

(22) Filed: Oct. 31, 2022

(65) Prior Publication Data

US 2023/0145870 A1    May 11, 2023

Related U.S. Application Data

(60) Provisional application No. 63/278,184, filed on Nov. 11, 2021.

(51) Int. Cl.

| | |
|---|---|
| *A61K 8/46* | (2006.01) |
| *A61K 8/25* | (2006.01) |
| *A61K 8/73* | (2006.01) |
| *A61K 8/898* | (2006.01) |
| *A61K 8/92* | (2006.01) |
| *A61Q 5/00* | (2006.01) |
| *A61Q 5/02* | (2006.01) |
| *A61Q 5/12* | (2006.01) |

(52) U.S. Cl.
CPC .............. *A61K 8/463* (2013.01); *A61K 8/25* (2013.01); *A61K 8/737* (2013.01); *A61K 8/898* (2013.01); *A61K 8/922* (2013.01); *A61Q 5/002* (2013.01); *A61Q 5/02* (2013.01); *A61Q 5/12* (2013.01); *A61K 2800/48* (2013.01)

(58) Field of Classification Search
CPC .......... A61K 8/463; A61K 8/25; A61K 8/737; A61K 8/898; A61K 8/922; A61K 2800/48; A61K 8/37; A61K 8/42; A61K 8/44; A61K 8/604; A61K 8/608; A61K 8/894; A61K 8/92; A61Q 5/002; A61Q 5/02; A61Q 5/12

See application file for complete search history.

(56) References Cited

U.S. PATENT DOCUMENTS

| | | | |
|---|---|---|---|
| 4,051,234 A | 9/1977 | Gieske et al. | |
| 8,030,262 B2 | 10/2011 | Walters et al. | |
| 9,271,908 B2 | 3/2016 | Allef et al. | |
| 10,391,046 B2 | 8/2019 | Hartnett et al. | |
| 10,426,713 B2 | 10/2019 | Song et al. | |
| 10,980,726 B2 | 4/2021 | Schroeder et al. | |
| 2006/0079415 A1 | 4/2006 | Kozubal et al. | |
| 2011/0165106 A1 | 7/2011 | Molenda et al. | |
| 2018/0104166 A1* | 4/2018 | Lipinski | A61K 8/345 |
| 2019/0046441 A1 | 2/2019 | Buge et al. | |
| 2019/0307668 A1* | 10/2019 | Stricane | A61K 8/44 |
| 2019/0365623 A1 | 12/2019 | Botto et al. | |
| 2020/0206122 A1 | 7/2020 | Perner et al. | |
| 2020/0276099 A1 | 9/2020 | Robbins et al. | |
| 2020/0330351 A1* | 10/2020 | Kong | A61K 8/73 |
| 2021/0267867 A1 | 9/2021 | Park et al. | |

FOREIGN PATENT DOCUMENTS

| | | | |
|---|---|---|---|
| CN | 111888270 A | * | 11/2020 |
| CN | 113384494 A | * | 2/2021 |
| WO | 2000/071652 | | 11/2000 |
| WO | 2006/044296 | | 4/2006 |
| WO | 2007/095255 | | 8/2007 |
| WO | 2016/036423 | | 3/2016 |
| WO | 2017/055295 | | 4/2017 |
| WO | 2017/058594 | | 4/2017 |
| WO | 2020/126219 | | 6/2020 |
| WO | 2021/226171 | | 11/2021 |

OTHER PUBLICATIONS

Hallstar Beauty (2020, hallstarbeauty.com/ product/florasolvs-jojoba-120/) (Year: 2020).*
Esteban (2018 cosmeticaitalia.it/export/sites/ default/centro-studi/appuntamenti/cosmoprof/Carmen_Esteban_SANA-Bologna-0918.pdf) (Year: 2018).*
International Search Report and the Written Opinion of the International Searching Authority issued in International Application PCT/US2022/048366 dated Mar. 17, 2023.

* cited by examiner

*Primary Examiner* — Lezah Roberts
*Assistant Examiner* — Abdulrahman Abbas

(57) ABSTRACT

Hair care compositions and methods for using the same are disclosed herein. According to one aspect of the disclosure, a hair care composition is provided that includes from about 1 to about 20 wt. % of an anionic surfactant; from about 0.5 to about 5 wt. % of an amphoteric surfactant; from about 0.1 to about 7 wt. % of a nonionic surfactant; from about 0.1 to about 5 wt. % of a thickening agent, wherein the thickening agent is a natural gum; and from about 0.05 to about 4.5 wt. % of a silicone wherein the hair composition is an emulsion and all weight percentages are based on the total weight of the hair care composition. Additionally, the hair care composition may have a weight ratio for the total amount of anionic surfactant to the total amount of amphoteric surfactant that is about 5:1 to about 20:1.

19 Claims, 6 Drawing Sheets

PERSONAL CARE COMPOSITIONS

CROSS-REFERENCE TO RELATED APPLICATION

This application claims the benefit of priority from U.S. Provisional Application No. 63/278,184, entitled "PERSONAL CARE COMPOSITIONS" and filed Nov. 11, 2021, the contents of which is hereby incorporated herein in its entirety.

BACKGROUND

The process of hair care is multifaceted and generally involves washing, conditioning, and styling the hair. The desirable results of the hair care process include a persistent look and feel of clean hair between washings, ease of combing, absence of static electricity, manageability, soft feel and shine. A limited number of hair care products are available which clean as well as condition the hair by the use of one product, i.e., a two-in-one conditioning shampoo. Certain two-in-one conditioning shampoos typically contain water, anionic surfactants, foam stabilizers, insoluble non-volatile silicone conditioning agents and silicone suspending agents.

Many two-in-one conditioning shampoos fail to repair and/or nourish damaged hair. Damaged hair is characterized by unnatural changes to the protein structure of the individual hair strands or shafts. Damage results in split ends, dry straw-like hair, hair that is easily broken, and hair that is "frizzy" and unmanageable. Because the visible portion of hair is dead, it has no ability to regenerate itself.

Accordingly, there is an ongoing need for improved hair care products that clean, condition, repair and/or nourish hair, including damaged hair.

BRIEF SUMMARY

In some embodiments, the present invention provides hair care compositions that include from about 1 to about 20 wt. % of an anionic surfactant; from about 0.5 to about 5 wt. % of an amphoteric surfactant; from about 0.1 to about 7 wt. % of a nonionic surfactant; from about 0.1 to about 5 wt. % of a thickening agent, wherein the thickening agent is a natural gum; and from about 0.05 to about 4.5 wt. % of a silicone wherein the hair composition is an emulsion and all weight percentages are based on the total weight of the hair care composition. Additionally, the hair care composition may have a weight ratio for the total amount of anionic surfactant to the total amount of amphoteric surfactant that is about 5:1 to about 20:1.

In further embodiments, the present invention provides a hair care composition that has from about 1 to about 20 wt. % of an anionic surfactant; from about 0.5 to about 5 wt. % of a betaine surfactant; from about 0.1 to about 7 wt. % of nonionic surfactants comprising brassica amido propyl dimethyl amine; from about 0.1 to about 10 wt. % of one or more fatty ester comprising PEG-120 jojoba; and from about 0.05 to about 4.5 wt. % of silicone, wherein all weight percentages are based on the total weight of the hair care composition. The hair care composition may have a weight ratio for the total amount of anionic surfactant to the total amount of amphoteric surfactant that is about 5:1 to about 20:1. Additionally, the hair care composition may have a weight ratio of brassica amido propyl dimethyl amine to PEG-120 jojoba that is from about 1:10 to about 10:1.

In additional embodiments, the present invention provides a hair care composition that includes from about 1 to about 20 wt. % of an anionic surfactant; from about 0.5 to about 5 wt. % of a betaine surfactant; from about 0.1 to about 10 wt. % of one or more fatty ester comprising isoamyl laurate; from about 0.1 to about 10 wt. % of one or more fatty ether comprising PPG-3 caprylyl ether; from about 0.05 to about 4.5 wt. % of silicone, wherein all weight percentages are based on the total weight of the hair care composition. The hair care composition may have a weight ratio for the total amount of anionic surfactant to the total amount of amphoteric surfactant that is about 5:1 to about 20:1. Additionally, the hair care composition may have a weight ratio of isoamyl laurate to PPG-3 caprylyl ether that is from about 1:10 to about 10:1.

In some embodiments, the hair care composition comprises one or more of about 1 to about 20 wt. % of sodium lauryl ether sulfate, about 0.1 to about 7 wt. % of cocoamidopropyl betaine, about 0.1 to about 7 wt. % of decyl glucoside and/or coco monoethanolamide, about 0.1 to about 7 wt. % of brassica amido propyl dimethyl amine, about 0.1 to about 10 wt. % of PEG-120 jojoba, about 0.1 to about 7 wt. % of ethylene glycol mono/di-stearate, about 0.1 to about 7 wt. % of isoamyl laurate, about 0.1 to about 7 wt. % of PPG-3 caprylyl ether, about 0.05 to about 4.5 wt. % of dimethiconol, bis-cetearyl, about 0.1 to about 5 wt. % of cationic guar and/or hydroxypropyl guar hydroxypropyltrimonium chloride, about 0.1 to about 10 wt. % of jojoba wax PEG120 esters, and water, wherein the weight ratio of the anionic surfactant to the betaine surfactant is about 5:1 to about 20:1. Additionally, the hair care composition may have a weight ratio of brassica amido propyl dimethyl amine to PEG-120 jojoba that is from about 1:10 to about 10:1 and/or a weight ratio of isoamyl laurate to PPG-3 caprylyl ether is from about 1:10 to about 10:1.

BRIEF DESCRIPTION OF THE DRAWINGS

The features, and advantages of the invention will be apparent from the following more detailed description of certain embodiments of the invention and as illustrated in the accompanying drawings in which.

Figure 1:
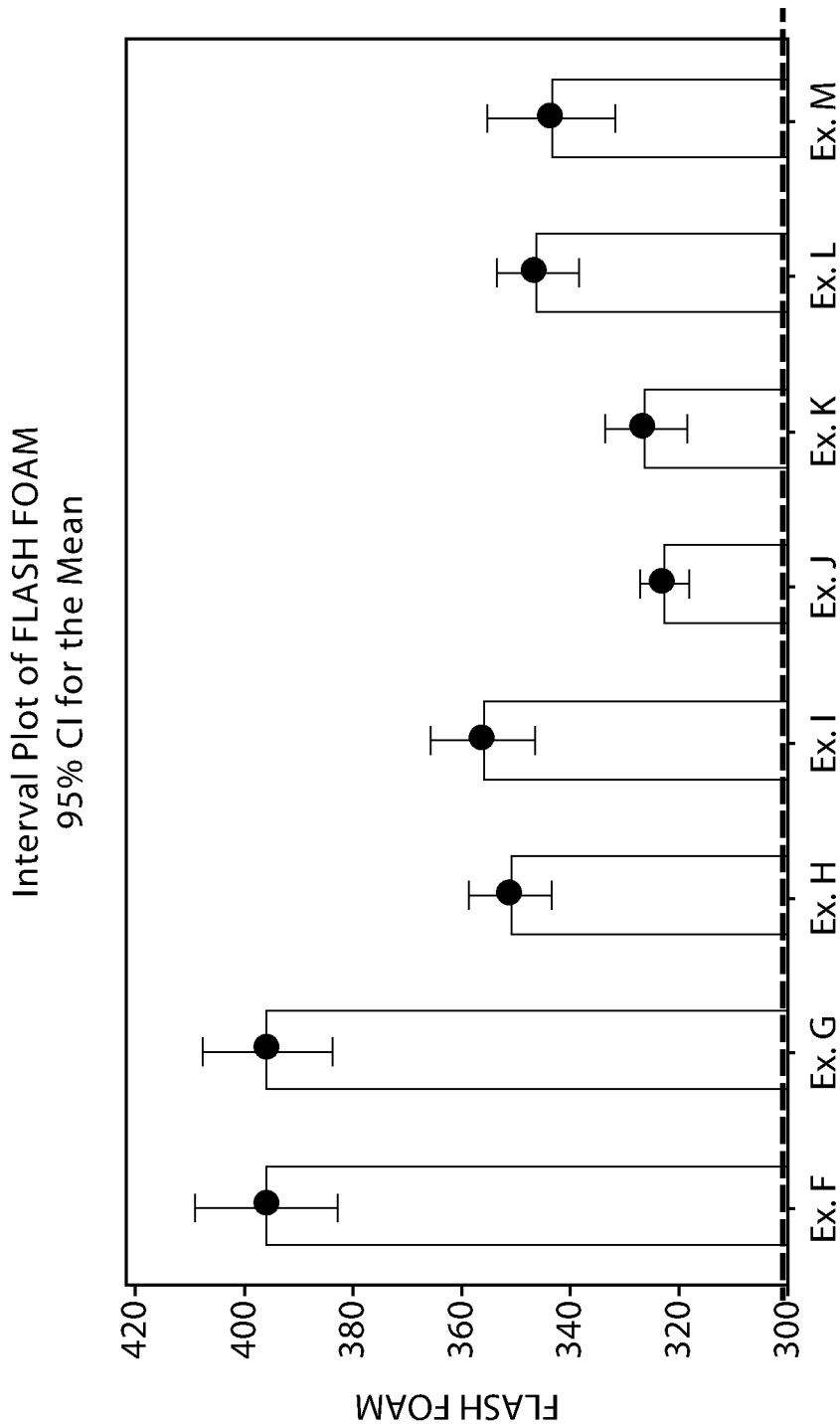
FIG. 1 is a bar graph of the flash foam of hair care compositions in accordance with aspects of the invention.

It should be understood that the various aspects are not limited to the compositions, arrangements, and instrumentality shown in the figures.

DETAILED DESCRIPTION

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other apparatuses and methods. Before explaining the disclosed embodiments of the present invention in detail, it is to be understood that the invention is not limited in its application to the details of any particular embodiment shown. The terminology used herein is for the purpose of description and not of limitation.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range. Thus, a range from 1-5, includes specifically 1, 2, 3, 4 and 5, as well as subranges such as 2-5, 3-5, 2-3, 2-4, 1-4, etc.

The term "about" when referring to a number means any number within a range of 10% of the number. For example, the phrase "about 2.0 wt. %" refers to a number between and including 1.8 wt. % and 2.2 wt. %.

All references cited herein are hereby incorporated by reference in their entireties. In the event of a conflict in a definition in the present disclosure and that of a cited reference, the present disclosure controls.

The abbreviations and symbols as used herein, unless indicated otherwise, take their ordinary meaning. The abbreviation "wt. %" means percent by weight with respect to the hair care composition. The symbol "°" refers to a degree, such as a temperature degree or a degree of an angle. The symbols "h", "min", "mL", "nm", "µm" refer to hour, minute, milliliter, nanometer, and micrometer, respectively.

When referring to chemical structures, and names, the symbols "C", "H", and "O" mean carbon, hydrogen, and oxygen, respectively. The symbols "—", "=" and "≡" mean single bond, double bond, and triple bond, respectively.

"Volatile", as used herein, means having a flash point of less than about 100° C. "Non-volatile", as used herein, means having a flash point of greater than about 100° C.

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

All components and elements positively set forth in this disclosure can be negatively excluded from the claims. In other words, the hair care compositions of the instant disclosure can be free or essentially free of all components and elements positively recited throughout the instant disclosure. In some instances, the hair care compositions of the present invention may be substantially free of non-incidental amounts of the ingredient(s) or compound(s) described herein. A non-incidental amount of an ingredient or compound is the amount of that ingredient or compound that is added into the hair care composition by itself. For example, a hair care composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the hair care composition includes both components (or the composition includes more than two components that overlap), an overlapping compound does not represent more than one component. For example, certain compounds may be characterized as both an emulsifier and a surfactant. If a particular hair care composition includes both an emulsifier and a surfactant, a compound that may be characterized as both an emulsifier and a surfactant will serve only as either an emulsifier or a surfactant—not both.

For readability purposes, chemical functional groups may be mentioned in their adjective form; for each of the adjectives, the word "group" should be assumed. For example, the adjective "alkyl" without a nouns thereafter, should be read as "an alkyl group".

Aspects of the present invention relate to hair care compositions and, particularly, hair care compositions that both clean and condition the hair. Additional aspects of the present invention relate to methods for using the hair care compositions disclosed herein.

The hair care compositions disclosed herein advantageously provide improved conditioning effects in conjunction with cleansing effects, while using a high content of natural ingredients. The present inventors discovered that certain combinations of fatty esters, fatty ethers, and nonionic surfactants in specific ratios provide hair care compositions having enhanced conditioning attributes. For instance, the inventors discovered that certain combinations of fatty esters and fatty ethers in specific ratios provide enhanced conditioning properties. Additionally, certain combinations of fatty esters and nonionic surfactants in specific ratios provide enhanced conditioning properties.

Surprisingly, the enhanced conditioning attributes may be achieved in some embodiments even with significantly reduced amounts of silicones. For instance, some embodiments of the invention utilize specific combinations of ingredients in specific ratios to provide superior conditioning attributes for wet hair relative to dry hair, while further embodiments provide superior conditioning attributes for dry hair relative to wet hair.

It was unexpected that embodiments of the invention could be obtained having a naturality index of 90% or more, based on ISO standard 16128, while having a reduced amount of silicone and simultaneously achieving superior conditioning and cleansing effects by employing the specific combination of ingredients at specific ratios disclosed herein.

In accordance with one embodiment, provided is a hair care composition comprising from about 1 to about 20 wt. % of an anionic surfactant; from about 0.5 to about 5 wt. % of an amphoteric surfactant; from about 0.1 to about 7 wt. % of a nonionic surfactant; from about 0.1 to about 5 wt. % of a thickening agent, wherein the thickening agent is a natural gum; and from about 0.05 to about 4.5 wt. % of a silicone, wherein the hair composition is an emulsion and all weight percentages are based on the total weight of the hair care composition. Additionally, the hair care composition may have a weight ratio for the total amount of anionic surfactant to the total amount of amphoteric surfactant that is about 5:1 to about 20:1.

As noted above, the hair care compositions may have a reduced amount of silicone. For instance, the hair care compositions have a total amount of silicone of about 4.5 wt. % or less, based on the total weight of the hair care composition. For instance, the hair care composition may have a total amount of silicone of about 3 wt. % or less, about 2 wt. % or less, about 1 wt. % or less, about 0.5 wt. % or less, or about 0.1 wt. % or less, based on the total weight of the hair care composition. In one embodiment, the hair care composition is free of or essentially free of silicone. In some embodiments, the hair care composition has an amount of silicone up to about 4.5 wt. %. For example, the hair care composition may have about 0.1 up to 4.5 wt. %, about 0.1 up to 3 wt. %, about 0.1 up to 2 wt. %, about 0.1 up to 1 wt. %; about 0.5 up to 4.5 wt. %, about 0.5 up to 3 wt. %, about 0.5 up to 2 wt. %, about 0.5 up to 1 wt. %; about 1 up to 4.5 wt. %, about 1 up to 3 wt. %, about 1 up to 2 wt. %, or any range or subrange thereof, based on the total weight of the hair care composition.

Preferably, the hair care compositions have a naturality index of about 90% or more, by weight of the total weight of the hair care composition, based on ISO standard 16128. In some embodiments, the hair care compositions have a naturality index of about 92% or more, about 94% or more, about 95% or more, about 96% or more, about 97% or more, about 98% or more, or about 99% or more, by weight of the total weight of the hair care composition, based on ISO standard 16128.

The hair care composition may have a weight ratio of the total amount of nonionic surfactant to the total amount of fatty ester that is from about 1:10 to about 10:1, about 1:9 to about 9:1, about 1:8 to about 8:1, from about 1:7 to about 7:1, about 1:6 to about 6:1, from about 1:5 to about 5:1, about 1:4 to about 4:1, about 1:3 to about 3:1, or from about 1:2 to about 2:1.

In some embodiments, the hair care composition includes one or more nonionic surfactant(s) comprising brassica amido propyl dimethyl amine and one or more fatty ester(s) comprising PEG-120 jojoba. The hair care compositions may have a weight ratio of brassica amido propyl dimethyl amine to PEG-120 Jojoba that is from about 1:10 to about 10:1, about 1:9 to about 9:1, about 1:8 to about 8:1, from about 1:7 to about 7:1, about 1:6 to about 6:1, from about 1:5 to about 5:1, about 1:4 to about 4:1, about 1:3 to about 3:1, or from about 1:2 to about 2:1.

Additionally or alternatively, the hair care composition may have a weight ratio of the total amount of fatty ester to the total amount of fatty ether that is from about 1:10 to about 10:1, about 1:9 to about 9:1, about 1:8 to about 8:1, from about 1:7 to about 7:1, about 1:6 to about 6:1, from about 1:5 to about 5:1, about 1:4 to about 4:1, about 1:3 to about 3:1, or from about 1:2 to about 2:1.

In some instances, the hair care composition includes one or more fatty ester(s) comprising isoamyl laurate and one or more fatty ether(s) comprising PPG-3 caprylyl ether. The hair care composition may have a weight ratio of isoamyl laurate to PPG-3 caprylyl ether that is from about 1:10 to about 10:1, about 1:9 to about 9:1, about 1:8 to about 8:1, from about 1:7 to about 7:1, about 1:6 to about 6:1, from about 1:5 to about 5:1, about 1:4 to about 4:1, about 1:3 to about 3:1, or from about 1:2 to about 2:1.

The hair care compositions may have a viscosity from about 1,000 to about 30,000 mPas (cps), such as from about 1,000 to about 25,000 mPas (cps) or about 7,000 to about 15,000 mPas (cps), measured at a temperature of 25° C. using spindle no. 4 at 10 rpm during 1 minute with a Brookfield viscometer. For instance, the hair care composition may have a viscosity from about 1,000 to about 30,000 mPas (cps), about 1,000 to about 25,000 mPas (cps), about 1,000 to about 20,000 mPas (cps), about 1,000 to about 17,000 mPas (cps), about 1,000 to about 15,000 mPas (cps); about 4,000 to about 30,000 mPas (cps), about 4,000 to about 25,000 mPas (cps), about 4,000 to about 20,000 mPas (cps), about 4,000 to about 17,000 mPas (cps), about 4,000 to about 15,000 mPas (cps); about 7,000 to about 30,000 mPas (cps), about 7,000 to about 25,000 mPas (cps), about 7,000 to about 20,000 mPas (cps), about 7,000 to about 17,000 mPas (cps), or about 7,000 to about 15,000 mPas (cps), measured at a temperature of 25° C. using spindle no. 4 at 10 rpm during 1 minute with a Brookfield viscometer.

The hair care compositions may have an emulsion. Although the hair care composition is preferably an oil-in-water emulsion, the hair care composition may be a water-in-oil emulsion in some embodiments. Additionally or alternatively, the hair care composition may be a shampoo, e.g., a conditioning shampoo, such as a 2-in-1 conditioner shampoo.

In some embodiments, the hair care composition comprises one or more of about 1 to about 20 wt. % of sodium lauryl ether sulfate, about 0.1 to about 7 wt. % of cocoamidopropyl betaine, about 0.1 to about 7 wt. % of decyl glucoside and/or coco monoethanolamide, about 0.1 to about 7 wt. % of brassica amido propyl dimethyl amine, about 0.1 to about 10 wt. % of PEG-120 jojoba, about 0.1 to about 7 wt. % of ethylene glycol mono/di-stearate, about 0.1 to about 7 wt. % of isoamyl laurate, about 0.1 to about 7 wt. % of PPG-3 caprylyl ether, about 0.05 to about 4.5 wt. % of dimethiconol, bis-cetearyl, about 0.1 to about 5 wt. % of cationic guar and/or hydroxypropyl guar hydroxypropyltrimonium chloride, about 0.1 to about 10 wt. % of jojoba wax PEG120 esters, and water. Additionally, the hair care composition may have a weight ratio of brassica amido propyl dimethyl amine to PEG-120 jojoba that is from about 1:10 to about 10:1 and/or a weight ratio of isoamyl laurate to PPG-3 caprylyl ether is from about 1:10 to about 10:1.

Suitable components, such as those listed below, may be included or excluded from the formulations for the hair care compositions depending on the specific combination of other components, the form of the hair care compositions, and/or the use of the formulation (e.g., a gel, cream, etc.).

The hair care compositions may include a surfactant system in an amount that may vary, but generally is in the range of from about 2 to about 40 wt. %, based on the total weight of the hair care composition. For example, the hair care composition may include about 2 to about 40 wt. %, about 2 to about 35 wt. %, about 2 to about 30 wt. %, about 2 to about 25 wt. %, about 2 to about 20 wt. %, about 2 to about 18 wt. %, about 2 to about 16 wt. %, about 2 to about 14 wt. %, about 2 to about 12 wt. %, about 2 to about 10 wt. %; about 5 to about 40 wt. %, about 5 to about 35 wt. %, about 5 to about 30 wt. %, about 5 to about 25 wt. %, about 5 to about 20 wt. %, about 5 to about 18 wt. %, about 5 to about 16 wt. %, about 5 to about 14 wt. %, about 5 to about 12 wt. %, about 5 to about 10 wt. %; about 7.5 to about 40 wt. %, about 7.5 to about 35 wt. %, about 7.5 to about 30 wt. %, about 7.5 to about 25 wt. %, about 7.5 to about 20 wt. %, about 7.5 to about 18 wt. %, about 7.5 to about 16 wt. %, about 7.5 to about 14 wt. %, about 7.5 to about 12 wt. %; about 10 to about 40 wt. %, about 10 to about 35 wt. %, about 10 to about 30 wt. %, about 10 to about 25 wt. %, about 10 to about 20 wt. %, about 10 to about 18 wt. %, about 10 to about 16 wt. %, about 10 to about 14 wt. %, about 10 to about 12 wt. %, including ranges and subranges thereof, based on the total weight of the hair care composition.

The surfactant systems disclosed herein typically comprise two or more surfactants selected from anionic surfactants, nonionic surfactants, amphoteric surfactants, zwitterionic surfactants, and combinations of two or more thereof. For instance, the surfactant system may include two or more surfactants, with the two or more surfactants being chosen from different categories of anionic surfactants, nonionic surfactants, amphoteric surfactants, and zwitterionic surfactants.

The hair care compositions include one or more anionic surfactant(s) in an amount of, e.g., from about 1 to about 20 wt. % of an anionic surfactant, based on the total weight of the hair care composition. In some embodiment, the amount of anionic surfactant present in the hair care composition is from about 1 to about 18 wt. %, about 1 to about 16 wt. %, about 1 to about 14 wt. %, about 1 to about 12 wt. %, about 1 to about 10 wt. %, about 1 to about 8 wt. %; about 2 to about 20 wt. %, about 2 to about 18 wt. %, about 2 to about 16 wt. %, about 2 to about 14 wt. %, about 2 to about 12 wt. %, about 2 to about 10 wt. %, about 2 to about 8 wt. %; about 3 to about 20 wt. %, about 3 to about 18 wt. %, about 3 to about 16 wt. %, about 3 to about 14 wt. %, about 3 to about 12 wt. %, about 3 to about 10 wt. %, about 3 to about 8 wt. %; about 4 to about 20 wt. %, about 4 to about 18 wt. %, about 4 to about 16 wt. %, about 4 to about 14 wt. %, about 4 to about 12 wt. %, about 4 to about 10 wt. %, about 4 to about 8 wt. %; about 5 to about 20 wt. %, about 5 to about 18 wt. %, about 5 to about 16 wt. %, about 5 to about 14 wt. %, about 5 to about 12 wt. %, about 5 to about 10 wt. %, or about 5 to about 8 wt. %, including all ranges and subranges thereof, based on the total weight of the hair care composition.

Anionic surfactants that may be useful herein include water-soluble salts of alkyl sulfates and alkyl ether sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium laurel ether sulfate (SEES), sodium lauryl sulfate, and sodium coconut monoglyceride sulfonates are examples of anionic surfactants of this type. Other suitable anionic surfactants are sarcosinates, such as sodium lauroyl sarcosinate, laurates, sodium lauryl sulfoacetate, sodium lauroyl isethionate, sodium laureth carboxylate, and sodium dodecyl benzenesulfonate. In one embodiment, the anionic surfactant comprises sodium laureth sulfate, sodium lauryl ether sulfate, sodium pareth sulfate, or a combination of two or more thereof.

In one embodiment, the hair care composition includes a sodium lauryl ether sulfate. The sodium lauryl ether sulfate may have an average ethoxylation of about 1 to about 5 mole per mole of lauryl ether sulfate group. In some instance, the average ethoxylation of the sodium lauryl ether sulfate is about 1 to about 4, about 1 to about 3, about 1 to about 2, or about 1 mole per mole of lauryl ether sulfate group.

Mixtures of anionic surfactants can also be employed. For instance, a variety of anionic surfactants can be utilized in the hair care composition including, for example, long chain alkyl ($C_6$-$C_{22}$) materials such as long chain alkyl sulfates, long chain alkyl sulfonates, long chain alkyl phosphates, long chain alkyl ether sulfates, long chain alkyl alpha olefin sulfonates, long chain alkyl taurates, long chain alkyl isethionates (SCI), long chain alkyl glyceryl ether sulfonates (AGES), sulfosuccinates, or combinations of two or more thereof. These anionic surfactants can be alkoxylated, for example, ethoxylated, although alkoxylation is not required. These surfactants are typically highly water soluble as their sodium, potassium, alkyl and ammonium or alkanol ammonium containing salt form and can provide high foaming cleansing power. Other equivalent anionic surfactants may be used in some cases.

The hair care compositions may include one or more amphoteric surfactant(s) in an amount that typically ranges from about 0.1 to about 7 wt. %, based on the total weight of the hair care composition. For example, the hair care composition may include one or more amphoteric surfactant(s) in an amount of from about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %, about 0.75 to about 1 wt. %; about 1 to about 7 wt. %, about 1 to about 6 wt. %, about 1 to about 5 wt. %, about 1 to about 4 wt. %, about 1 to about 3 wt. %, or about 1 to about 2 wt. %, including ranges and subranges thereof, based on the total weight of the hair care composition.

Amphoteric surfactants are typically characterized by a combination of high surfactant activity, lather forming and mildness. The amphoteric surfactant may comprise a substituent containing 8 to 18 carbon atoms and a substituent containing one or more carboxylate, sulfonate, sulfate, phosphate, or phosphonate. The amphoteric surfactant(s) may include, but are not limited to, derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used in some cases.

Additional examples of amphoteric surfactants include, but are not limited to, a range of betaines including, for example, high alkyl betaines, such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups, such as the cocamidopropyl and cocoamidoethyl betaines. In at least one embodiment, the betaine surfactant is selected from cocamidopropyl betaine, lauryl dimethyl betaine, cetyl dimethyl betaine, and cocoamphodiacetate, and a combination of two or more thereof.

Mixtures of amphoteric surfactants can also be employed. Further examples of suitable amphoteric surfactants include sultaines, also known as sulfobetaines, and hydroxy sultaines, for example, cocamidopropyl hydroxysultain. Additional amphoteric surfactants and nonionic surfactants can be found in U.S. Pat. No. 4,051,234, which is incorporated herein in its entirety for all purposes.

Additionally or alternatively, the hair care composition may include an amphoteric surfactant selected from alkyl sultaines, alkyl amphoacetates, alkyl amphodiacetates, alkyl amphopropionates, and combinations of two or more thereof. The alkyl group of the alkyl sultaines, alkyl amphoacetates, alkyl amphodiacetates, and/or alkyl amphopropionates may comprise 8 to 18 carbons, e.g., 8 to 16 carbons, 8 to 12 carbons, or 8 to 11 carbons. Examples of alkyl sultaines include cocamidopropyl hydroxysultaine, lauryl hydroxysultaine, and mixtures of two or more thereof. Non-limiting examples of alkyl amphopropionates include cocoamphopropionate, cornamphopropionatecaprylamphopropionate, cornamphopropionate, caproamphopropionate, oleoamphopropionate, isostearoamphopropionate, stearoamphopropionate, lauroamphopropionate, salts thereof, and a mixture of two or more thereof.

The hair care compositions may include one or more nonionic surfactant(s) in an amount that typically ranges from about 0.1 to about 7 wt. %, based on the total weight of the hair care composition. For instance, the hair care composition may include one or more nonionic surfactant(s) in an amount of from about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 7 wt. %, about 1 to about 6 wt. %, about 1 to about 5 wt. %, about 1 to about 4 wt. %, about 1 to about 3 wt. %, about 1 to about 2 wt. %; about 1.5 to about 7 wt. %, about 1.5 to about 6 wt. %, about 1.5 to about 5 wt. %, about 1.5 to about 4 wt. %, about 1.5 to about 3 wt. %; about 2 to about 7 wt. %, about 2 to about 6 wt. %, about 2 to about 5 wt. %, about 2 to about 4 wt. %, about 2 to about 3 wt. %; about 3 to about 7 wt. %, about 3 to about 6 wt. %, about 3 to about 5 wt. %, or about 3 to about 4 wt. %, including ranges and subranges thereof, based on the total weight of the hair care composition.

The nonionic surfactant may be selected from an alkanolamide, a glucoside, a fatty amine, a polyether, and a combination of two more thereof. For instance, the hair care composition may include a glucoside selected from arachidyl glucoside, $C_{12-20}$ alkyl glucoside, caprylyl/capryl glucoside, cetearyl glucoside, coco-glucoside, lauryl glucoside, decyl glucoside, or a combination of two more thereof. In some instances, the nonionic surfactant is selected from decyl glucoside, PEG-120 methyl glucose dioleate, coco monoethanolamide, bras sica amido propyl dimethyl amine, and a combination of two more thereof. In further instances, the nonionic surfactant comprises two or more of decyl glucoside, PEG-120 methyl glucose dioleate, coco monoethanolamide, and brassica amido propyl dimethyl amine.

Examples of nonionic surfactants that may, in some cases, be suitably incorporated into the hair care composition include and/or may be chosen from alkylphenols and esters of fatty acids, being ethoxylated, propoxylated or glycerolated and having at least one fatty chain comprising, e.g., from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may be made of copolymers of ethylene oxide and/or of propylene oxide; condensates of ethylene oxide and/or of propylene oxide with fatty alcohols; polyethoxylated fatty amides comprising, e.g., from 2 to 30 mol of ethylene oxide; polyglycerolated fatty amides comprising, e.g., from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; N-($C_6$-$C_{24}$)alkylglucamine derivatives, amine oxides such as ($C_{10}$-$C_{14}$)alkylamine oxides or N-($C_{10}$-$C_{14}$)acylaminopropylmorpholine oxides; and a combination of two or more thereof.

The nonionic surfactants may, additionally or alternatively, be chosen from those broadly defined as compounds produced by the condensation of alkylene oxide groups (hydrophilic in nature) with an organic hydrophobic compound which may be aliphatic or alkyl-aromatic in nature. Other examples of suitable nonionic surfactants include but are not limited to monoethanol amides, for example, alkyl monoethanolamides, such as cocomonoethanolamide, lauramide monoethanolamide, and the like. Further examples of suitable nonionic surfactants include poloxamers (sold under trade name PLURONIC®), polyoxyethylene, polyoxyethylene sorbitan esters (sold under trade name TWEENS®), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, alkyl polyglycosides (for example, fatty alcohol ethers of polyglycosides, such as fatty alcohol ethers of polyglucosides, e.g., decyl, lauryl, capryl, caprylyl, myristyl, stearyl and other ethers of glucose and polyglucoside polymers, including mixed ethers such as capryl/caprylyl glucoside, coco glucoside, and lauryl glucoside), long chain tertiary amine oxides, long chain tertiary phosphine oxides, long chain dialkyl sulfoxides, and mixtures of such materials. For example, the acyl glucamides may be chosen from lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, tocopheryl succinate methylglucamide, and combinations of two or more thereof.

Additional examples of nonionic surfactants include polysorbate 20, long chain alkyl glucosides having $C_8$-$C_{22}$ alkyl groups; coconut fatty acid monoethanolamides such as cocamide MEA; coconut fatty acid diethanolamides; fatty alcohol ethoxylates (alkylpolyethylene glycols); alkylphenol polyethylene glycols; alkyl mercaptan polyethylene glycols; fatty amine ethoxylates (alkylaminopolyethylene glycols); fatty acid ethoxylates (acylpolyethylene glycols); polypropylene glycol ethoxylates (for example the PLURONIC™ block copolymers commercially available from BASF); fatty acid alkylolamides, (fatty acid amide polyethylene glycols); N-alkyl-, N-alkoxypolyhydroxy fatty acid amides; sucrose esters; sorbitol esters; polyglycol ethers; and combinations of two or more thereof.

The nonionic surfactant may include fatty acid alkanolamides, such as those formed by reacting an alkanolamine and a $C_6$-$C_{36}$ fatty acid. Examples thereof include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and combinations of two or more thereof.

Cationic surfactants can, optionally, be included in the composition. The cationic surfactant, when present, is typically included in the hair care composition in an amount of from about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %, about 0.75 to about 1 wt. %; about 1 to about 7 wt. %, about 1 to about 6 wt. %, about 1 to about 5 wt. %, about 1 to about 4 wt. %, about 1 to about 3 wt. %, or about 1 to about 2 wt. %, including ranges and subranges thereof, based on the total weight of the hair care composition.

The term "cationic surfactant" means a surfactant that may be positively charged when it is contained in the hair care compositions according to the present disclosure. The cationic surfactant may bear one or more positive permanent charges or may contain one or more functional groups that are cationizable in the hair care composition according to the present disclosure.

The one or more cationic surfactants, if present, may include or be chosen from quaternary ammonium compounds, amidoamines, and combinations of two or more thereof. Examples of cationic surfactants that may be suitable for the hair care composition include or may be chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and a combination of two or more thereof.

Additional, non-limiting examples of cationic surfactants include: cetyl trimethyl ammonium chloride available, for example, with trade name CA-2350 from Nikko Chemicals and CTAC 30KC available from KCI, stearyl trimethyl ammonium chloride with trade name Arquad 18/50 available from Akzo Nobel, hydrogenated tallow alkyl trimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl (myristylacetate) ammonium chloride, and N-(stearoyl colamino formyl methy) pyridinium chloride.

Hydrophilically substituted cationic surfactants in which at least one of the substituents contain one or more aromatic, ether, ester, amido, or amino moieties present as substituents or as linkages in the chain may also be in the hair care composition. Non-limiting examples of hydrophilically substituted cationic surfactants that may be useful in the hair care compositions include the materials having the following INCI designations: quaternium-16, quaternium-26, quaternium-27, quaternium-30, quaternium-33, quaternium-43, quaternium-52, quaternium-53, quaternium-56, quaternium-60, quaternium-61, quaternium-62, quaternium-70, quaternium-71, quaternium-72, quaternium-75, quaternium-76 hydrolyzed collagen, quaternium-77, quaternium-78, quaternium-79 hydrolyzed collagen, quaternium-79 hydrolyzed keratin, quaternium-79 hydrolyzed milk protein, quaternium-79 hydrolyzed silk, quaternium-79 hydrolyzed soy protein, and quaternium-79 hydrolyzed wheat protein, quaternium-80, quaternium-81, quaternium-82, quaternium-83, quaternium-84, or a combination of two or more thereof.

In certain instances, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and a combination of two or more thereof. In some cases, the cationic surfactant is selected from cetrimonium chloride, behentrimonium chloride, and a combination of two or more thereof.

The hair care composition may include one or more fatty ester(s). The one or more fatty ester(s) may be present in the hair care composition in an amount of from about 0.1 to about 10 wt. %, based on the total weight of the hair care composition. For instance, the one or more fatty ester(s) may be present in an amount of about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %; about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %; about 0.75 to about 10 wt. %, about 0.75 to about 9 wt. %, about 0.75 to about 8 wt. %, about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; about 1.5 to about 10 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %, about 2 to about 3 wt. %; about 3 to about 10 wt. %, about 3 to about 9 wt. %, about 3 to about 8 wt. %, about 3 to about 7 wt. %, about 3 to about 6 wt. %, about 3 to about 5 wt. %; about 4 to about 10 wt. %, about 4 to about 9 wt. %, about 4 to about 8 wt. %, about 4 to about 7 wt. %, or about 4 to about 6 wt. %, including ranges and subranges thereof, based on the total weight of the hair care composition.

The one or more fatty ester(s) may be selected from isoamyl caprylate, isoamyl caprinate, isoamyl caprate, isoamyl laurate, isoamyl myristate, isoamyl palmitate, isoamyl stearate, isoamyl oleate, isoamyl linolate, isoamyl linoleate, isoamyl behenate, ethylhexyl stearate, hexadecyl stearate, hexyl laurate, isoamyl laurate, PEG-120 jojoba, and a combination of two more thereof. In some embodiments, the hair care composition includes 2, 3, 4, 5, 6, 7, or 8 fatty esters, including any range or subrange therebetween. Preferably, the hair care composition comprises PEG-120 jojoba, isoamyl laurate, or a combination thereof.

The hair care composition may include one or more fatty ether(s). In some embodiments, the hair care composition includes 2, 3, 4, 5, 6, 7, or 8 fatty ethers, including any range or subrange therebetween. The one or more fatty ether(s) may be present in the hair care composition in an amount of from about 0.1 to about 10 wt. %, based on the total weight of the hair care composition. For instance, the one or more fatty ether(s) may be present in an amount of about 0.1 to about 10 wt. %, about 0.1 to about 9 wt. %, about 0.1 to about 8 wt. %, about 0.1 to about 7 wt. %, about 0.1 to about 6 wt. %, about 0.1 to about 5 wt. %, about 0.1 to about 4 wt. %, about 0.1 to about 3 wt. %, about 0.1 to about 2 wt. %; about 0.5 to about 10 wt. %, about 0.5 to about 9 wt. %, about 0.5 to about 8 wt. %, about 0.5 to about 7 wt. %, about 0.5 to about 6 wt. %, about 0.5 to about 5 wt. %, about 0.5 to about 4 wt. %, about 0.5 to about 3 wt. %, about 0.5 to about 2 wt. %; about 0.75 to about 10 wt. %, about 0.75 to about 9 wt. %, about 0.75 to about 8 wt. %, about 0.75 to about 7 wt. %, about 0.75 to about 6 wt. %, about 0.75 to about 5 wt. %, about 0.75 to about 4 wt. %, about 0.75 to about 3 wt. %, about 0.75 to about 2 wt. %; about 1 to about 10 wt. %, about 1 to about 9 wt. %, about 1 to about 8 wt. %, about 1 to about 7 wt. %, about 1 to about 6 wt. %, about 1 to about 5 wt. %, about 1 to about 4 wt. %, about 1 to about 3 wt. %, about 1 to about 2 wt. %; about 1.5 to about 10 wt. %, about 1.5 to about 9 wt. %, about 1.5 to about 8 wt. %, about 1.5 to about 7 wt. %, about 1.5 to about 6 wt. %, about 1.5 to about 5 wt. %, about 1.5 to about 4 wt. %, about 1.5 to about 3 wt. %; about 2 to about 10 wt. %, about 2 to about 9 wt. %, about 2 to about 8 wt. %, about 2 to about 7 wt. %, about 2 to about 6 wt. %, about 2 to about 5 wt. %, about 2 to about 4 wt. %, about 2 to about 3 wt. %; about 3 to about 10 wt. %, about 3 to about 9 wt. %, about 3 to about 8 wt. %, about 3 to about 7 wt. %, about 3 to about 6 wt. %, about 3 to about 5 wt. %; about 4 to about 10 wt. %, about 4 to about 9 wt. %, about 4 to about 8 wt. %, about 4 to about 7 wt. %, or about 4 to about 6 wt. %, including ranges and subranges thereof, based on the total weight of the hair care composition.

The hair care composition may include a fatty ether phosphoric acid, a fatty ether carboxylic acid, or a combination of thereof. Non-limiting examples of fatty ether phosphoric acids compounds include those corresponding to formulas IV and V:

$$RO[CH_2O]_u[(CH_2)_xCH(R')(CH_2)_y(CH_2)_zO]_v[CH_2CH_2O]_w\text{—PO—}(OH)_2 \quad \text{Formula IV,}$$

$$\{RO[CH_2O]_u[(CH_2)_xCH(R')(CH_2)_y(CH_2)_zO]_v[CH_2CH_2O]_w\}_2PO\text{—}(OH) \quad \text{Formula V}$$

wherein
R is a hydrocarbon radical containing from about 6 to about 40 carbon atoms;
u, v and w, independently of one another, represent numbers of from 0 to 60;
x, y and z, independently of one another, represent numbers of from 0 to 13;
R' represents hydrogen, alkyl, and
the sum of x+y+z being ≥0.

The references, "u," "v," and "w" each represent the degree of alkoxylation. Whereas, on a molecular level, the references "u," "v," and "w" and the total degree of alkoxylation can only be integers, including zero, on a macroscopic level they are mean values in the form of broken numbers. In formulas IV and V, "R" is linear of branched, acyclic or cyclic, saturated or unsaturated, aliphatic or aromatic, substituted or unsubstituted, typically a linear or branched, acyclic $C_{6-40}$ alkyl or alkenyl group or a $C_{1-40}$ alkyl phenyl group, more typically a $C_{8-22}$ alkyl or alkenyl group or a $C_{4-18}$ alkyl phenyl group, even more typically a $C_{12-18}$ alkyl group or alkenyl group or a $C_{6-16}$ alkyl phenyl group; "u," "v," "w," independently of one another, is typically a number from 2 to 20, more typically a number from 3 to 17 and most typically a number from 5 to 15; "x," "y," "z," independently of one another, is typically a number from 2 to 13, more typically a number from 1 to 10 and most typically a number from 0 to 8.

Non-limiting examples of fatty ether carboxylic acids include butoxynol-5 carboxylic acid, butoxynol-19 carboxylic acid, capryleth-4 carboxylic acid, capryleth-6 carboxylic acid, capryleth-9 carboxylic acid, ceteareth-25 carboxylic acid, coceth-7 carboxylic acid, $C_{9-11}$ pareth-6 carboxylic acid, $C_{11-15}$ pareth-7 carboxylic acid, $C_{12-13}$ pareth-5 carboxylic acid, $C_{12-13}$ pareth-8 carboxylic acid, $C_{12-13}$ pareth-12 carboxylic acid, $C_{12-15}$ pareth-7 carboxylic acid, $C_{12-15}$ pareth-8 carboxylic acid, $C_{14-15}$ pareth-8 carboxylic acid, deceth-7 carboxylic acid, laureth-3 carboxylic acid, laureth-4 carboxylic acid, laureth-5 carboxylic acid, laureth-6 carboxylic acid, laureth-8 carboxylic acid, laureth-10 carboxylic acid, laureth-11 carboxylic acid, laureth-12 carboxylic acid, laureth-13 carboxylic acid, laureth-14 carboxylic acid, laureth-17 carboxylic acid, ppg-6-laureth-6 carboxylic acid, ppg-8-steareth-7 carboxylic acid, myreth-3 carboxylic acid, myreth-5 carboxylic acid, nonoxynol-5 carboxylic acid, nonoxynol-8 carboxylic acid, nonoxynol-10 carboxylic acid, octeth-3 carboxylic acid, octoxynol-20 carboxylic acid, oleth-3 carboxylic acid, oleth-6 carboxylic acid, oleth-10 carboxylic acid, PPG-3-deceth-2 carboxylic acid, capryleth-2 carboxylic acid, ceteth-13 carboxylic acid, deceth-2 carboxylic acid, hexeth-4 carboxylic acid, isosteareth-6 carboxylic acid, isosteareth-11 carboxylic acid, trudeceth-3 carboxylic acid, trideceth-6 carboxylic acid, trideceth-8 carboxylic acid, trideceth-12 carboxylic acid, trideceth-3 carboxylic acid, trideceth-4 carboxylic acid, trideceth-7 carboxylic acid, trideceth-15 carboxylic acid, trideceth-19 carboxylic acid, undeceth-5 carboxylic acid, or a combination of two or more thereof. In some embodiment, the fatty ether phosphoric acid comprises PPG-5-ceteth-10 phosphate, oleth-3 phosphate, oleth-10 phosphate, dicetyl phosphate, PPG-3 caprylyl ether, or a combination of two or more thereof.

Further examples of fatty ether phosphoric acids include PPG-5-Ceteth-10 phosphate (CRODAFOS SG), Oleth-3 phosphate (CRODAFOS N3 acid), Oleth-10 phosphate (CRODAFOS N10 acid), and a mixture of Ceteth-10 phosphate and Dicetyl phosphate (CRODAFOS CES) all sold by Croda.

The hair care compositions include one or more thickening agent(s), typically in an amount of about 0.1 to 5 wt. %, based on the total weight of the hair care composition. For example, the thickening agent may be present in the hair care composition in an amount of from about 0.1 to 5 wt. %, about 0.1 to 4 wt. %, about 0.1 to 3 wt. %, about 0.1 to 2 wt. %, about 0.1 to 1 wt. %; about 0.3 to 5 wt. %, about 0.3 to 4 wt. %, about 0.3 to 3 wt. %, about 0.3 to 2 wt. %, about 0.3 to 1 wt. %; about 0.5 to 5 wt. %, about 0.5 to 4 wt. %, about 0.5 to 3 wt. %, about 0.5 to 2 wt. %, about 0.5 to 1 wt. %; about 0.75 to 5 wt. %, about 0.75 to 4 wt. %, about 0.75 to 3 wt. %, about 0.75 to 2 wt. %, about 0.75 to 1 wt. %; about 1 to 5 wt. %, about 1 to 4 wt. %, about 1 to 3 wt. %, about 1 to 2 wt. %; about 2 to 5 wt. %, about 2 to 4 wt. %, or about 2 to 3 wt. %, including ranges and subranges thereof, based on the total weight of the hair care composition.

Thickening agents may be referred to as "thickeners" or "viscosity modifying agents." Thickening agents are typically included to increase the viscosity of the hair care compositions. Nonetheless, in some instances, certain thickening agents provide additional, surprising benefits to the hair care compositions. Non-limiting examples of thickening agents include natural gums, polyacrylate crosspolymers or crosslinked polyacrylate polymers, cationic acrylate copolymers, anionic acrylic or carboxylic acid polymers, polyacrylamide polymers, polysaccharides such as cellulose derivatives, cationic gums, polyquaterniums, vinylpyrrolidone homopolymers/copolymers, $C_{8-24}$ hydroxyl substituted aliphatic acid, $C_{8-24}$ conjugated aliphatic acid, sugar fatty esters, polyglyceryl esters, and a mixture thereof. Particular types of thickening agents that may be mentioned include the following: gums, sucrose esters, polyvinylpyrrolidone (PVP) and co-polymers, celluloses, polyquaternium compounds, and carboxylic acid or carboxylate based homopolymer or co-polymer, which can be linear or crosslinked.

The thickening agent of the hair care composition may be a natural gum. For instance, the thickening agent may be selected from gum arabic, tragacanth gum, karaya gum, guar gum, gellan gum, tara gum, locust bean gum, tamarind gum, xanthan gum, locust bean gum, Seneca gum, sclerotium gum, gellan gum, etc. In some embodiments, the natural gum is selected from hydroxypropyl guar gum, xanthan gum, sclerotium gum, cationic guar, hydroxypropyl guar hydroxypropyltrimonium chloride, and a combination of two more thereof.

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

Additionally or alternatively, the hair care compositions may include one or more thickeners including, but are not limited to, polyvinyl pyrrolidone, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, and the like, and mixtures or combinations of two or more thereof. In one embodiment, the hair care composition includes a thickening system comprising a polymer selected from polyvinyl pyrrolidone, a polyacrylate, a polymethacrylate, a polyitaconate, an acrylamide, 2-acrylamido-2-methylpropane sulfonic acid (AMPS), and a combination of two or more thereof.

The hair care compositions may, optionally, include one or more silicone(s) in an amount that typically ranges from about 0.05 to about 4.5 wt. %, based on the total weight of the hair care composition. For instance, the hair care composition may include one or more silicone(s) in an amount of from about 0.05 to about 4 wt. %, about 0.05 to about 3 wt. %, about 0.05 to about 2 wt. %, about 0.05 to about 1 wt. %; about 0.1 to about 4.5 wt. %, about 0.1 to about 4 wt. %, about 0.1 to about 3 wt. %, about 0.1 to about 2 wt. %, about 0.1 to about 1 wt. %; about 0.5 to about 4.5 wt. %, about 0.5 to about 4 wt. %, about 0.5 to about 3 wt. %, about 0.5 to about 2 wt. %, about 0.5 to about 1 wt. %; about 1 to about 4.5 wt. %, about 1 to about 4 wt. %, about 1 to about 3 wt. %, about 1 to about 2 wt. %; about 1.5 to about 4.5 wt. %, about 1.5 to about 4 wt. %, about 1.5 to about 3 wt. %; about 2 to about 4.5 wt. %, about 2 to about 4 wt. %, about 2 to about 3 wt. %; about 3 to about 4.5 wt. %, or about 3 to about 4 wt. %, including ranges and subranges thereof, based on the total weight of the hair care composition.

The one or more silicone(s) may be chosen from amino-functionalized silicones. The term "amino-functionalized silicone" or "amino silicones" means a silicone containing at least one primary amino, secondary amino, tertiary amino and/or quaternary ammonium group. The structure of the amino-functionalized silicone may be linear or branched, cyclic or non-cyclic. The amino functional group may be at any position in the silicone molecule, preferably at the end of the backbone (for example, in the case of amodimethicones) and/or in the side chain.

Non-limiting examples of silicones include amine-functionalized silicones (e.g., amodimethicone), dimethicone, bis-aminopropyl dimethicone, trimethyl silylamodimethicone, dimethicone copolyols, etc. The hair care composition may include, in some instances, one or more silicones chosen from polydimethylsiloxanes (dimethicones), polydiethylsiloxanes, polydimethyl siloxanes having terminal hydroxyl groups (dimethiconols), polymethylphenylsiloxanes, phenylmethylsiloxanes, amino functional polydimethylsiloxane (amodimethicone), bis-aminopropyl dimethicone, trimethylsilylamodimethicone, dimethicone copolyols, dimethicone copolyol esters, dimethicone copolyol quaternium nitrogen containing compounds, dimethicone copolyol phosphate esters, and mixtures thereof. For example, the one or more silicones may be or include one or more dimethicone copolyols. The copolyols may be chosen from Dimethicone PEG-8 Adipate, Dimethicone PEG-8 Benzoate, Dimethicone PEG-7 Phosphate, Dimethicone PEG-10 Phosphate, Dimethicone PEG/PPG-20/23 Benzoate, Dimethicone PEG/PPG-7/4 Phosphate, Dimethicone PEG/PPG-12/4 Phosphate, PEG-3 Dimethicone, PEG-7 Dimethicone, PEG-8 Dimethicone, PEG-9 Dimethicone, PEG-10 Dimethicone, PEG-12 Dimethicone, PEG-14 Dimethicone, PEG-17 Dimethicone, PEG/PPG-3/10 Dimethicone, PEG/PPG-4/12 Dimethicone, PEG/PPG-6/11

Dimethicone, PEG/PPG-8/14 Dimethicone, PEG/PPG-14/4 Dimethicone, PEG/PPG-15/15 Dimethicone, PEG/PPG-16/2 Dimethicone, PEG/PPG-17/18 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and a mixture thereof.

In some cases, the silicones, optionally, include or are chosen from siloxanes having an organo functional group, such as polyalkylsiloxanes, where at least one alkyl radical is different than methyl, for example organopolysiloxanes having the INCI name Stearyl Dimethicone, Cetyl Dimethicone or C26-28 Alkyl Dimethicone, or, for example, polyarylsiloxanes and polyarylalkylsiloxanes, for example organopolysiloxanes having the INCI name Phenyl Trimethicone, Trimethylsiloxyphenyl Dimethicone or Dimethylphenyl Dimethicone, or, for example, organopolysiloxanes having an organofunctional radical such as an aminopropyl, aminopropyl-aminoethyl, aminopropyl-aminoisobutyl radical, for example organopolysiloxanes having the INCI name Amodimethicone, or, for example, organopolysiloxanes having a polyethylene glycol or polyalkylene glycol radical, for example organopolysiloxanes having the INCI name PEG-12 Dimethicone, PEG/PPG-25,25-Dimethicone or Cetyl PEG/PPG-15/15 Butyl Ether Dimethicone. In one embodiment, the hair care composition comprises dimethiconol, bis-cetearyl amodimethicone and ceteareth, or a combination thereof.

The hair care compositions may, optionally, include a cationic polymer. In some cases, the hair care compositions include a cationic polymer in an amount of from about 0.01 to about 5 wt. %, about 0.01 to about 4 wt. %, about 0.01 to about 3 wt. %, about 0.01 to about 2 wt. %, about 0.01 to about 1 wt. %; about 0.05 to about 5 wt. %, about 0.05 to about 4 wt. %, about 0.05 to about 3 wt. %, about 0.05 to about 2 wt. %, about 0.05 to about 1 wt. %; about 0.1 to about 5 wt. %, about 0.1 to about 4 wt. %, about 0.1 to about 3 wt. %, about 0.1 to about 2 wt. %, about 0.1 to about 1 wt. %; about 0.5 to about 5 wt. %, about 0.5 to about 4 wt. %, about 0.5 to about 3 wt. %, about 0.5 to about 2 wt. %, or about 0.5 to about 1 wt. %, including ranges and subranges thereof, based on the total weight of the hair care composition.

The cationic polymers may be homopolymers or formed from two or more types of monomers. The molecular weight of the polymer may be between 5,000 and 10,000,000, typically at least 10,000, and preferably in the range 100,000 to about 2,000,000. These polymers will typically have cationic nitrogen containing groups such as quaternary ammonium or protonated amino groups, or a mixture thereof. The cationic charge density is suitably at least 0.1 meq/g, preferably above 0.8 or higher. In some instances, the cationic charge density does not exceed 3 meq/g, or does not exceed 2 meq/g. The charge density can be measured using the Kjeldahl method and can be within the above limits at the desired pH of use, which will in general be from about 3 to 9 and preferably between 4 and 8.

Non-limiting examples of cationic polymers include, for example, copolymers of vinyl monomers having cationic amine or quaternary ammonium functionalities with water soluble spacer monomers, such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol, and ethylene glycol.

The cationic amines can be primary, secondary, or tertiary amines, depending upon the particular species and the pH of the composition. Amine substituted vinyl monomers and amines can be polymerized in the amine form and then converted to ammonium by quaternization. Suitable cationic amino and quaternary ammonium monomers include, for example, vinyl compounds substituted with dialkyl amincalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings, such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably $C_1$ and $C_2$ alkyls. Additional amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$, alkyls.

The cationic conditioning polymers can comprise mixtures of monomer units derived from amine- and/or quaternary ammonium-substituted monomer and/or compatible spacer monomers. Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, and combinations of two or more thereof. In some cases, preferred polyquaternium compounds include polyquaternium-10, polyquaternium-11, polyquaternium-67, and a combination of two or more thereof.

Other cationic conditioning polymers that can be used include cationic guar gum derivatives, such as guar hydroxypropyltrimonium chloride or hydroxypropyl guar hydroxypropyltrimmonium chloride. In some instances, the hair care compositions include one or more cationic conditioning polymers selected from cationic cellulose derivatives, quaternized hydroxyethyl cellulose (e.g., polyquaternium-10), cationic starch derivatives, cationic guar gum derivatives (guar hydroxypropyltrimonium chloride or hydroxypropyl guar hydroxypropyltrimmonium chloride), copolymers of acrylamide and dimethyldiallyammonium chloride (e.g., polyquaternium-7), polyquaterniums, and a combination of two or more thereof.

Additionally or alternatively, the hair care composition may include one or more oils. In some cases, the hair care composition includes oil in an amount of from about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %; about 0.05 to about 10 wt. %, about 0.05 to about 8 wt. %, about 0.05 to about 6 wt. %, about 0.05 to about 5 wt. %, about 0.05 to about 4 wt. %, about 0.05 to about 3 wt. %, about 0.05 to about 2 wt. %, about 0.05 to about 1 wt. %; about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %; about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; about 1 to about 10 wt. %, about 1 to about 8 wt. %, about 1 to about 6 wt. %, about 1 to about 5 wt. %, about 1 to about 4 wt. %, about 1 to about 3 wt. %; about 2 to about 10 wt. %, about 2 to about 8 wt. %, about 2 to about 6 wt. %, about 2 to about 5 wt. %, about 2 to about 4 wt. %; about 3 to about 10 wt. %, about 3 to about 8 wt. %, about 3 to about 6 wt. %, about 3 to about 5 wt. %; about 4 to about 10 wt. %, about 4 to about 8 wt. %, about 4 to about 6 wt. %, about 4 to about 5 wt. %; about 6 to about 10 wt. %, or about 6 to about 8 wt. %, including ranges and subranges thereof, based on the total weight of the hair care composition.

The oil included in the hair care composition may be a natural based oil (e.g., an oil derived from a natural source). For example, the hair care composition may include natural oils of plant origin, such as amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, currant seed oil, jojoba oil, linseed oil, macadamia nut oil, corn oil, almond oil, marula oil, evening primrose oil, olive oil, palm oil, palm kernel oil, Brazil nut oil, pecan nut oil, peach kernel oil, rapeseed oil, castor oil, sea buckthorn pulp oil, sea buckthorn kernel oil, sesame oil, soy bean oil, sunflower oil, grape seed oil, walnut oil, wild rose oil, wheat germ oil, the liquid components of coconut oil, or a combination of two or more thereof. In one embodiment, the oil is a plant oil selected from palm oil, soybean oil, olive oil, coconut oil, and a combination of two or more thereof.

Non-limiting examples of vegetable oils include Abyssinian oil, Almond oil, Apricot oil, Apricot Kernel oil, Argan oil, Avocado oil, Babassu oil, Baobab oil, Black Cumin oil, Black Currant oil, Borage oil, Camelina oil, Carinata oil, Canola oil, Castor oil, Cherry Kernel oil, Coconut oil, Corn oil, Cottonseed oil, Echium oil, Evening Primrose oil, Flax Seed oil, Grape Seed oil, Grapefruit Seed oil, Hazelnut oil, Hemp Seed oil, Jatropha oil, Jojoba oil, Kukui Nut oil, Linseed oil, Macadamia Nut oil, Meadowfoam Seed oil, Moringa oil, Neem oil, Olive oil, Palm oil, Palm Kernel oil, Peach Kernel oil, Peanut oil, Pecan oil, Pennycress oil, Perilla Seed oil, Pistachio oil, Pomegranate Seed oil, Pongamia oil, Pumpkin Seed oil, Raspberry oil, Red Palm Olein, Rice Bran oil, Rosehip oil, Safflower oil, Seabuckthorn Fruit oil, Sesame Seed oil, Shea Olein, Sunflower oil, Soybean oil, Tonka Bean oil, Tung oil, Walnut oil, Wheat Germ oil, High Oleoyl Soybean oil, High Oleoyl Sunflower oil, High Oleoyl Safflower oil, High Erucic Acid Rapeseed oil, and a combination of two or more thereof. Non-limiting examples of animal fats include lard, tallow, chicken fat, yellow grease, fish oil, emu oil, combinations of these, and the like. Non-limiting example of a synthesized oil includes tall oil, which is a byproduct of wood pulp manufacture. In some embodiments, the natural oil is refined, bleached, and/or deodorized.

The hair care composition may further comprise one or more colorants. The colorants may be a pigment, a dye, or mixtures thereof. Non-limiting examples of pigments include titanium dioxide, zinc oxide, kaolin, mica etc. Non-limiting examples of dyes include food dyes suitable for food, drug and cosmetic applications, and mixtures thereof. Some color agents (colorants) are known as FD&C dyes. In some embodiments, the colorants may be present in an amount ranging from about 0.0001% wt. % to about 0.4% wt. %, including all percentages and subranges therebetween, based on the total weight of the hair care composition. In further embodiments, the colorants may be present in an amount ranging from about 0.0001% wt. % to about 4% wt. %, including all percentages and subranges therebetween, based on the total weight of the hair care composition.

The hair care composition may include one or more pH adjusters to increase or decrease the overall pH of the hair care composition. For example, one or more acids may be included to decrease the pH of the hair care composition. Examples of suitable acids for decreasing the pH of the hair care composition include, but are not limited to, citric acid, acetic acid, and the like. The hair care composition may include one or more bases, such as sodium hydroxide, potassium hydroxide and the like, to increase the pH of the hair care composition. Additional or alternative acids and bases that are suitable for adjusting the pH of the hair care composition are readily known to one of ordinary skill in the art.

The amount of the pH adjuster in the hair care composition may be based on the desired pH of the final hair care composition and/or product. For example, the total amount of the pH adjuster may range from about 0.05 to about 20 wt. %, based on the total weight of the hair care composition. In some instances, the total amount of pH adjuster is from about 0.05 to about 15 wt. %, about 0.1 to about 10 wt. %, or about 0.12 to about 5 wt. %, including ranges and sub-ranges therebetween, based on the total weight of the hair care composition.

As noted above, the hair care compositions may have a pH from 4.5 to about 10, 4.5 to about 9, 4.5 to about 8, 4.5 to about 7, 4.5 to about 6; about 5 to about 10, about 5 to about 9, about 5 to about 8, about 5 to about 7, about 5 to about 6; about 6 to about 10, about 6 to about 9, about 6 to about 8, or about 6 to about 7, including any ranges and subranges therebetween.

According to another aspect of the invention, provided are methods for cleaning and/or conditioning hair. Methods of treating hair according to the disclosure may vary but typically include applying a hair care composition as disclosed herein, allowing the hair care composition to remain on the hair for a sufficient amount of time, rubbing and/or massaging the hair care composition throughout the hair and, further optionally, rinsing the hair care compositions from the hair. The hair care composition may be applied to the hair in a sequence with other compositions. For example, the hair care composition may be applied to the hair before shampooing the hair, after shampooing the hair, before conditioning the hair, and/or after conditioning the hair, etc. The compositions, however, are not required to be used in a sequence.

The methods may include applying an amount of the hair care composition onto the user's hair, for example, onto one or both hands, onto the hair, etc. The user's hair may already be wet or damp with extraneous water or extraneous water can be included after the hair care composition has already been applied to the hair. The extraneous water typically has a temperature of about 25° to 50° C. The hair care composition may be applied to the user's hand(s) or directly to the hair while the user is showering and/or bathing in water having a temperature of, e.g., 25° to 50° C. The hair care composition may optionally be rinsed from the user's hair.

Non-limiting embodiments of certain aspects of the invention are discussed below to elucidate various combinations of features according to the disclosure herein. Additional combinations of features for embodiments of the invention are contemplated by inventors.

In accordance with embodiment 1, provided is a hair care composition comprising:
from about 1 to about 20 wt. % of an anionic surfactant;
from about 0.1 to about 7 wt. % of an amphoteric surfactant, wherein the weight ratio of a total amount of the anionic surfactant to the total amount of amphoteric surfactant is about 5:1 to about 20:1;
from about 0.1 to about 7 wt. % of a nonionic surfactant;
from about 0.1 to about 5 wt. % of a thickening agent; and
from about 0.05 to about 4.5 wt. % of a silicone,
wherein the hair composition is an emulsion and all weight percentages are based on the total weight of the hair care composition.

According to embodiment 2, the hair care composition of embodiment 1 wherein the emulsion is an oil-in-water emulsion.

According to embodiment 3, the hair care composition of embodiment 1 or embodiment 2 wherein the anionic surfactant comprises sodium lauryl ether sulfate.

According to embodiment 4, the hair care composition of embodiment 3 wherein the sodium lauryl ether sulfate has an average ethoxylation of about 1 mole per mole of lauryl ether sulfate group.

According to embodiment 5, the hair care composition of any foregoing embodiment wherein the amphoteric surfactant comprises a substituent containing 8 to 18 carbon atoms and a substituent containing one or more carboxylate, sulfonate, sulfate, phosphate, or phosphonate.

According to embodiment 6, the hair care composition of any foregoing embodiment wherein the amphoteric surfactant is a betaine surfactant.

According to embodiment 7, the hair care composition of embodiment 6 wherein the betaine surfactant comprises cocamidopropyl betaine, lauryl dimethyl betaine, cetyl dimethyl betaine, and cocoamphodiacetate, or a combination of two or more thereof.

According to embodiment 8, the hair care composition of any foregoing embodiment wherein the nonionic surfactant is selected from an alkanolamide, a glucoside, a fatty amine, a polyether, and a combination of two more thereof.

According to embodiment 9, the hair cosmetic composition of embodiment 8 wherein the glucoside is selected from arachidyl glucoside, C12-20 alkyl glucoside, caprylyl/capryl glucoside, cetearyl glucoside, coco-glucoside, lauryl glucoside, decyl glucoside, and a combination of two more thereof.

According to embodiment 10, the hair care composition of any foregoing embodiment, wherein the nonionic surfactant is selected from decyl glucoside, PEG-120 methyl glucose dioleate, coco monoethanolamide, brassica amido propyl dimethyl amine, and a combination of two more thereof.

According to embodiment 11, the hair care composition of any one of embodiments 1 to 8 wherein the nonionic surfactant comprises two or more of decyl glucoside, PEG-120 methyl glucose dioleate, coco monoethanolamide, and brassica amido propyl dimethyl amine.

According to embodiment 12, the hair care composition of any foregoing embodiment further comprising from about 1 to about 10 wt. % of a fatty ester.

According to embodiment 13, the hair care composition of embodiment 12 wherein the fatty ester is selected from isoamyl caprylate, isoamyl caprinate, isoamyl caprate, isoamyl laurate, isoamyl myristate, isoamyl palmitate, isoamyl stearate, isoamyl oleate, isoamyl linolate, isoamyl linoleate, isoamyl behenate, ethylhexyl stearate, hexadecyl stearate, hexyl laurate, isoamyl laurate, PEG-120 jojoba, and a combination of two more thereof.

According to embodiment 14, the hair care composition of any foregoing embodiment wherein the nonionic surfactant comprises brassica amido propyl dimethyl amine and the fatty ester comprises PEG-120 jojoba.

According to embodiment 15, the hair care composition of embodiment 14 wherein the hair care composition has a weight ratio of brassica amido propyl dimethyl amine to PEG-120 Jojoba of from about 1:10 to about 10:1, optionally from about 1:7 to about 7:1, optionally from about 1:5 to about 5:1, or optionally from about 1:2 to about 2:1.

According to embodiment 16, the hair care composition of any foregoing embodiment further comprising a fatty ether.

According to embodiment 17, the hair care composition of embodiment 16 wherein the fatty ether is selected from fatty ether phosphoric acids, fatty ether carboxylic acid, or a combination of thereof.

According to embodiment 18, the hair care composition of embodiment 16 or embodiment 17 wherein the fatty ether carboxylic acid comprises butoxynol-5 carboxylic acid, butoxynol-19 carboxylic acid, capryleth-4 carboxylic acid, capryleth-6 carboxylic acid, capryleth-9 carboxylic acid, ceteareth-25 carboxylic acid, coceth-7 carboxylic acid, C9-11 pareth-6 carboxylic acid, C11-15 pareth-7 carboxylic acid, C12-13 pareth-5 carboxylic acid, C12-13 pareth-8 carboxylic acid, C12-13 pareth-12 carboxylic acid, C12-15 pareth-7 carboxylic acid, C12-15 pareth-8 carboxylic acid, C14-15 pareth-8 carboxylic acid, deceth-7 carboxylic acid, laureth-3 carboxylic acid, laureth-4 carboxylic acid, laureth-5 carboxylic acid, laureth-6 carboxylic acid, laureth-8 carboxylic acid, laureth-10 carboxylic acid, laureth-11 carboxylic acid, laureth-12 carboxylic acid, laureth-13 carboxylic acid, laureth-14 carboxylic acid, laureth-17 carboxylic acid, ppg-6-laureth-6 carboxylic acid, ppg-8-steareth-7 carboxylic acid, myreth-3 carboxylic acid, myreth-5 carboxylic acid, nonoxynol-5 carboxylic acid, nonoxynol-8 carboxylic acid, nonoxynol-10 carboxylic acid, octeth-3 carboxylic acid, octoxynol-20 carboxylic acid, oleth-3 carboxylic acid, oleth-6 carboxylic acid, oleth-10 carboxylic acid, PPG-3-deceth-2 carboxylic acid, capryleth-2 carboxylic acid, ceteth-13 carboxylic acid, deceth-2 carboxylic acid, hexeth-4 carboxylic acid, isosteareth-6 carboxylic acid, isosteareth-11 carboxylic acid, trudeceth-3 carboxylic acid, trideceth-6 carboxylic acid, trideceth-8 carboxylic acid, trideceth-12 carboxylic acid, trideceth-3 carboxylic acid, trideceth-4 carboxylic acid, trideceth-7 carboxylic acid, trideceth-15 carboxylic acid, trideceth-19 carboxylic acid, undeceth-5 carboxylic acid, or a combination of two or more thereof.

According to embodiment 19, the hair care composition of embodiment 17 wherein the fatty ether phosphoric acid comprises PPG-5-ceteth-10 phosphate, oleth-3 phosphate, oleth-10 phosphate, dicetyl phosphate, PPG-3 caprylyl ether, or a combination of two or more thereof.

According to embodiment 20, the hair care composition of embodiment 1 further comprising isoamyl laurate and PPG-3 caprylyl ether.

According to embodiment 21, the hair care composition of embodiment 20 wherein the hair care composition has a weight ratio of isoamyl laurate to PPG-3 caprylyl ether of from about 1:10 to about 10:1, optionally from about 1:7 to about 7:1, optionally from about 1:5 to about 5:1, or optionally from about 1:2 to about 2:1.

According to embodiment 22, the hair care composition of any foregoing embodiment wherein the thickening agent is a natural gum.

According to embodiment 23, the hair care composition of any foregoing embodiment wherein the thickening agent comprises hydroxypropyl guar gum, xanthan gum, sclerotium gum, cationic guar, hydroxypropyl guar hydroxypropyltrimonium chloride, or a combination of two more thereof.

According to embodiment 24, the hair care composition of any foregoing embodiment further comprising from about 0.01 to about 5 wt. % of a cationic polymer.

According to embodiment 25, the hair care composition of embodiment 24 wherein the cationic polymer comprises a monomer selected from dialkyl amincalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, pyridinium, imidazolium, quaternized pyrrolidine, and a combination of two or more thereof.

According to embodiment 26, the hair care composition of embodiment 24 wherein the cationic polymer is a cationic cellulose derivative.

According to embodiment 27, the hair care composition of embodiment 26 wherein the cationic cellulose derivative is selected from guar hydroxypropyltrimonium chloride or hydroxypropyl guar hydroxypropyltrimmonium chloride.

According to embodiment 28, the hair care composition of embodiment 24 wherein the cationic polymer is a polyquaternium.

According to embodiment 29, the hair care composition of embodiment 24 or embodiment 28, wherein the polyquaternium is selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, and a combination of two or more thereof.

According to embodiment 30, the hair care composition of any of embodiments 24, 28, or 29, wherein the polyquaternium is polyquaternium-6.

According to embodiment 31, the hair care composition of any foregoing embodiment wherein the amount of silicone is from about 0.05 to about 3 wt. %.

According to embodiment 32, the hair care composition of 31 wherein the amount of silicone is from about 0.05 to about 1 wt. %.

According to embodiment 33, the hair care composition of any foregoing embodiment further comprising a cationic surfactant.

According to embodiment 34, the hair care composition of embodiment 33 wherein the cationic surfactant is selected from behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride, distearyldimonium chloride, dodecyl dimethyl ethylbenzyl ammonium chloride, Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and a combination of two or more thereof.

According to embodiment 35, the hair care composition of any foregoing embodiment further comprising from about 0.01 to about 10 wt. % of an oil.

According to embodiment 36, the hair care composition of embodiment 35 wherein the oil is a natural oil of plant origin.

According to an embodiment 37, provided is a hair care composition comprising:
  from about 1 to about 20 wt. % of an anionic surfactant;
  from about 0.1 to about 7 wt. % of a betaine surfactant, wherein the weight ratio of the anionic surfactant to the betaine surfactant is about 5:1 to about 20:1;
  from about 0.1 to about 7 wt. % of nonionic surfactants comprising brassica amido propyl dimethyl amine;
  from about 0.1 to about 10 wt. % of one or more fatty ester comprising PEG-120 jojoba, wherein the weight ratio of brassica amido propyl dimethyl amine to PEG-120 jojoba is from about 1:10 to about 10:1;
  from about 0.05 to about 4.5 wt. % of silicone, wherein all weight percentages are based on the total weight of the hair care composition.

According to embodiment 38, the hair care composition of embodiment 37 the weight ratio of brassica amido propyl dimethyl amine to PEG-120 Jojoba is from about 1:7 to about 7:1, optionally from about 1:5 to about 5:1, or optionally from about 1:2 to about 2:1.

According to embodiment 39, the hair care composition of embodiment 37 or embodiment 38, wherein the hair care composition has a naturality index of 90% or more, based on ISO standard 16128.

According to embodiment 40, the hair care composition of any of embodiments 37 to 39, wherein the betaine surfactant is selected from cocamidopropyl betaine, cocodimethylcarboxymethylbetaine, lauryldimethylcarboxymethylbetaine, lauryldimethylcarboxyethylbetaine, cetyldimethyl-carboxymethylbetaine, lauryl-bis-(2-hydroxyethyl)-carboxymethylbetaine, oleyldimethylgammacarboxypropylbetaine, and lauryl-bis-(2-hydroxypropyl)-carboxyethyl-betaine, and a combination of two or more thereof.

According to embodiment 41, provided is a hair care composition comprising:
from about 1 to about 20 wt. % of an anionic surfactant;
from about 0.1 to about 7 wt. % of a betaine surfactant, wherein the weight ratio of the anionic surfactant to the betaine surfactant is about 5:1 to about 20:1;
from about 0.1 to about 10 wt. % of one or more fatty ester comprising isoamyl laurate;
from about 0.1 to about 10 wt. % of one or more fatty ether comprising PPG-3 caprylyl ether,
wherein the weight ratio of isoamyl laurate to PPG-3 caprylyl ether is from about 1:10 to about 10:1; and
from about 0.05 to about 4.5 wt. % of silicone,
wherein all weight percentages are based on the total weight of the hair care composition.

According to embodiment 42, the hair care composition of embodiment 41 wherein the weight ratio of isoamyl laurate to PPG-3 caprylyl ether is from about 1:7 to about 7:1, optionally from about 1:5 to about 5:1, or optionally from about 1:2 to about 2:1.

According to embodiment 43, the hair care composition of any foregoing embodiment, wherein the silicone comprises dimethiconol.

EXAMPLES

Example 1

Five non-limiting, exemplary hair compositions (Example Compositions A-E) were prepared having the formulations shown in Table 1, below, in accordance with aspects of the invention.

TABLE 1

| US INCI Name | Ex. A (wt. %) | Ex. B (wt. %) | Ex. C (wt. %) | Ex. D (wt. %) | Ex. E (wt. %) |
| --- | --- | --- | --- | --- | --- |
| SODIUM LAURYL ETHER SULFATE (1EO) | 7.8 | 7.8 | 7.8 | 7.5 | 7.5 |
| COCOAMIDOPROPYL BETAINE | 0.6 | 0.6 | 0.6 | 0.6 | 0.6 |
| Weight ratio of anionic surfactant to amphoteric surfactant | 13:1 | 13:1 | 13:1 | 12.6:1 | 12.6:1 |
| DECYL GLUCOSIDE and COCO MONOETHANOLAMIDE | 2.6 | 2.8 | 2.8 | 2.6 | 2.6 |
| PEG-120 METHYL GLUCOSE DIOLEATE | 0.2 | | | | |
| BRASSICA AMIDO PROPYL DIMETHYL AMINE | 0.3 | | 0.3 | | |
| PEG-120 JOJOBA | 0.3 | | 0.3 | 0.1 | 0.1 |
| Weight ratio of brassica amido propyl dimethyl amine to PEG-120 jojoba | 1:1 | | 1:1 | | |
| ETHYLENE GLYCOL MONO/DI-STEARATE | 0.8 | 1 | 1 | 1 | 1 |
| ISOAMYL LAURATE | | ≤0.1 | | | |
| PPG-3 CAPRYLYL ETHER | | ≤0.1 | | | |
| Weight ratio of isoamyl laurate to PPG-3 caprylyl ether | | 1.14:1 | | | |
| POLYQUATERNIUM-6 (40%) | ≤0.05 | ≤0.05 | ≤0.05 | ≤0.05 | ≤0.05 |
| DIMETHICONOL | 1.2 | 1.2 | 1.2 | 1.4 | 1.4 |
| BIS-CETEARYL AMODIMETHICONE AND CETEARETH | | | | 0.4 | 0.4 |
| CATIONIC GUAR and/or HYDROXYPROPYL GUAR HYDROXYPROPYLTRIMONIUM CHLORIDE | 0.4 | 0.4 | 0.3 | 0.4 | 0.4 |
| HYDROLYZED KERATIN, ALMOND OIL, GRAPE SEED OIL AND ARGAN OIL, CAMELLIA OLIFEIRA SEED OIL EXTRACT, BIOTIN EXTRACT | | | | ≤0.5 | ≤0.1 |
| FRAGRANCE | 0.9 | 0.9 | 0.9 | 0.9 | 0.9 |
| ETHYLENEDIAMINETETRAACETIC ACID (EDTA), SODIUM BENZOATE, and/or SODIUM SALICYLATE | 0.4 | 0.4 | 0.4 | 0.4 | 0.4 |
| SODIUM DIHYDROGEN PHOSPHATE MONOHYDRATE | 0.3 | 0.3 | 0.3 | | |
| CITRIC ACID | 1 | 1 | 1 | 0.7 | 0.7 |
| CAUSTIC SODA | | | | | 0.1 |
| SODIUM CHLORIDE | 0.3 | 0.3 | 0.3 | 0.2 | 0.2 |
| Miscellaneous solvents, surfactants, and/or emulsifiers (e.g., ETHANOLAMINE, LAURETH-23, PEG-55 STEARATE, AND/OR LAURETH-4) | ≤0.5 | ≤0.5 | ≤0.5 | | |
| JOJOBA WAX PEG120 ESTERS | | | | 1 | 1 |
| WATER | Q.S. to 100 | Q.S. to 100 | Q.S. to 100 | Q.S. to 100 | Q.S. to 100 |

Example 2

Eight example hair care compositions (Ex. F-M) were prepared in accordance with the formulations provided in Table 2.

TABLE 2

| US INCI Name | Ex. F (wt. %) | Ex. G (wt. %) | Ex. H (wt. %) | Ex. I (wt. %) | Ex. J (wt. %) | Ex. K (wt. %) | Ex. L (wt. %) | Ex. M (wt. %) |
|---|---|---|---|---|---|---|---|---|
| SODIUM LAURYL ETHER SULFATE (1EO) | 7.8 | 7.8 | 7.8 | 7.8 | 7.8 | 7.8 | 7.8 | 7.8 |
| COCOAMIDOPROPYL BETAINE | 0.6 | 0.6 | 0.6 | 0.6 | 0.6 | 0.6 | 0.6 | 0.6 |
| Weight ratio of anionic surfactant to amphoteric surfactant | 13:1 | 13:1 | 13:1 | 13:1 | 13:1 | 13:1 | 13:1 | 13:1 |
| DECYL GLUCOSIDE and COCO MONOETHANOLAMIDE | 2.7 | 2.7 | 2.7 | 2.7 | 2.7 | 2.7 | 2.7 | 2.7 |
| BRASSICA AMIDO PROPYL DIMETHYL AMINE | | | 0.3 | 0.3 | 0.5 | 0.5 | | 0.3 |
| PEG 120 JOJOBA | 0.4 | 0.8 | 0.3 | 0.3 | | | | 0.3 |
| DIMETHICONOL | 1.2 | 1.2 | 1.2 | 1.2 | 1.2 | 1.2 | 1.2 | 1.2 |
| ISOAMYL LAURATE | | | | | | ≤0.1 | ≤0.1 | |
| PPG3 CAPRYLYL ETHER | | | | | | ≤0.1 | ≤0.1 | |
| Weight ratio of isoamyl laurate to PPG-3 caprylyl ether | | | | | | 1.14:1 | 1.14:1 | |
| ETHYLENE GLYCOL MONO/DI-STEARATE | 0.8 | 0.8 | 0.8 | 0.8 | 0.8 | 0.8 | 0.8 | 0.8 |
| POLYQUATERNIUM-6 | ≤0.05 | ≤0.05 | ≤0.05 | ≤0.05 | ≤0.05 | ≤0.05 | ≤0.05 | ≤0.05 |
| CATIONIC GUAR and/or HYDROXYPROPYL GUAR | 0.4 | 0.4 | 0.4 | 0.3 | 0.4 | 0.4 | 0.4 | 0.3 |
| WATER | Q.S. to 100 | Q.S. to 100 | Q.S. to 100 | Q.S. to 100 | Q.S. to 100 | Q.S. to 100 | Q.S. to 100 | Q.S. to 100 |

Example 3

Example Compositions F-M were evaluated to assess the various properties and attributes provided by such compositions. A benchmark conditioning shampoo (Comparative Composition 1), having the formulation provided in Table 3, was also evaluated under the same procedures as Compositions F-M.

TABLE 3

| US INCI Name | Comp. 1 (wt. %) |
|---|---|
| SODIUM LAURETH SULFATE | 8.47 |
| COCOAMIDOPROPYL BETAINE | 0.9 |
| Weight ratio of anionic surfactant to amphoteric surfactant | 9.4:1 |
| COCO MONOETHANOLAMIDE | 1.8 |
| ETHYLENE GLYCOL MONO/DI-STEARATE | 1.3 |
| POLYQUATERNIUM-6 | ≤0.05 |
| DIMETHICONOL | 2.1 |
| ORGANOMODIFIED CATIONIC POLYSILOXANE | ≤0.1 |
| CATIONIC GUAR | 0.4 |
| HYDROLYZED KERATIN, Almond oil, Grape Seed oil, Argan oil, CAMELLIA OLIFEIRA SEED OIL EXTRACT, and BIOTIN EXTRACT | 0.4 |
| FRAGRANCE | 0.9 |
| ETHYLENEDIAMINETETRAACETIC ACID (EDTA) | 0.2 |
| SODIUM BENZOATE and SODIUM SALICYLATE | 0.3 |
| SODIUM DIHYDROGEN PHOSPHATE MONOHYDRATE | 0.3 |
| CITRIC ACID | 0.5 |
| SODIUM CHLORIDE | 0.6 |
| Miscellaneous solvents, surfactants, and/or emulsifiers (e.g., ETHANOLAMINE, LAURETH-23, PEG-55 STEARATE, LAURETH-4, and/or Na$_2$O CAUSTIC SODA) | ≤0.5 |
| WATER | Q.S. to 100 |

Figure 2:
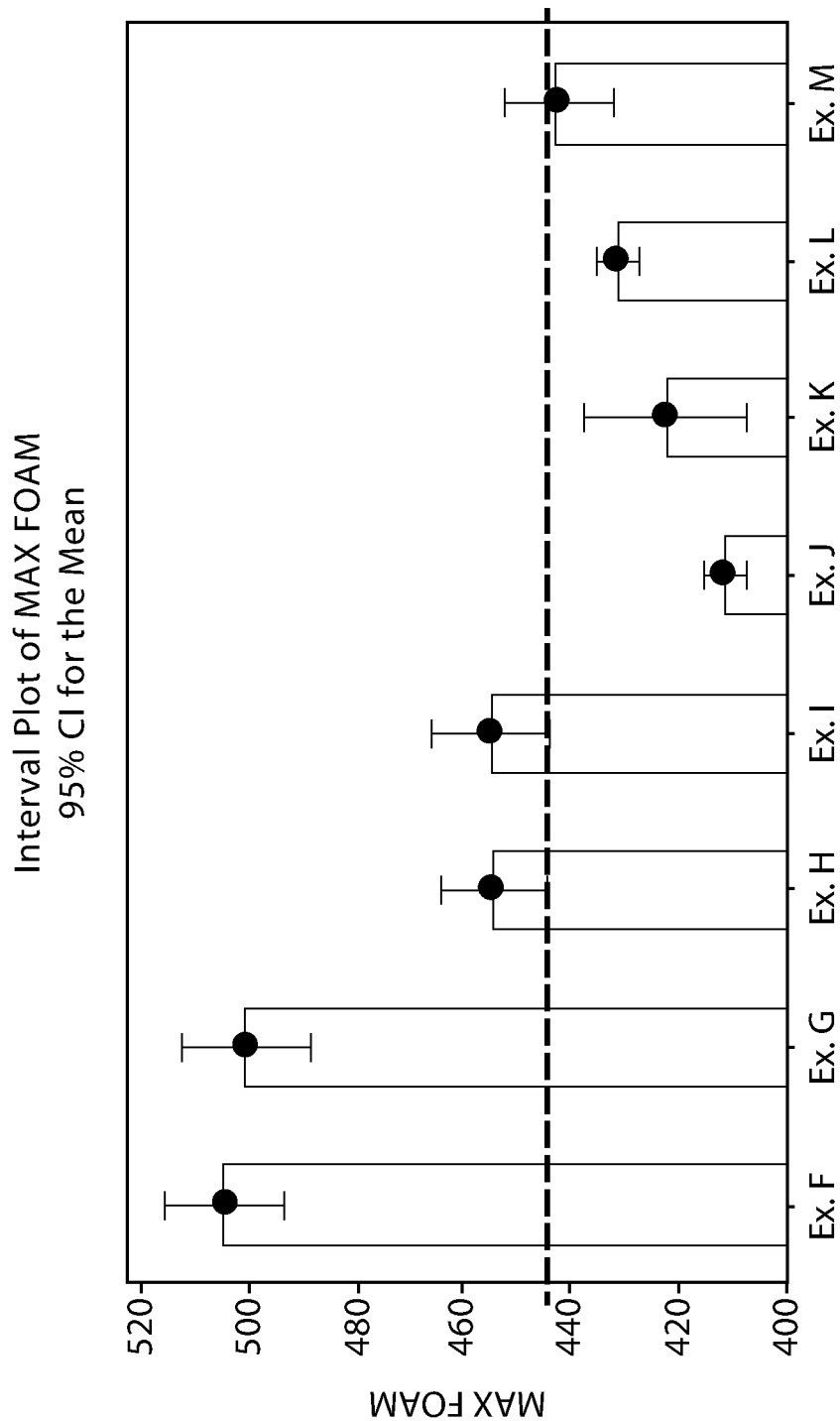
FIG. 2 is a bar graph of the max foam of hair care compositions in accordance with aspects of the invention.

Specifically, Compositions F-M and a Comparative Composition 1 (Comp. 1) were evaluated for flash foam, max foam, viscosity, density, instability, detangling, and combing force properties. Flash and max foam was measured for each of Example Compositions F-M and Comparative Composition 1 at a temperature of about 23° C. using 100 mL aqueous solutions formed from the respective compositions. Each of the aqueous solutions had a formulation of 1 wt. % of the respective compositions with the remainder of the composition being water. The aqueous solutions were subsequently put inside a 500 mL test tube and agitated with controlled rotational 180° vertical movements in a Gaum foam shaker apparatus. Flash foam was determined as the foam volume after 8 agitation cycles while the max foam was determined as the foam volume after 14 agitation cycles (see FIGS. 1 and 2).

Figure 3:
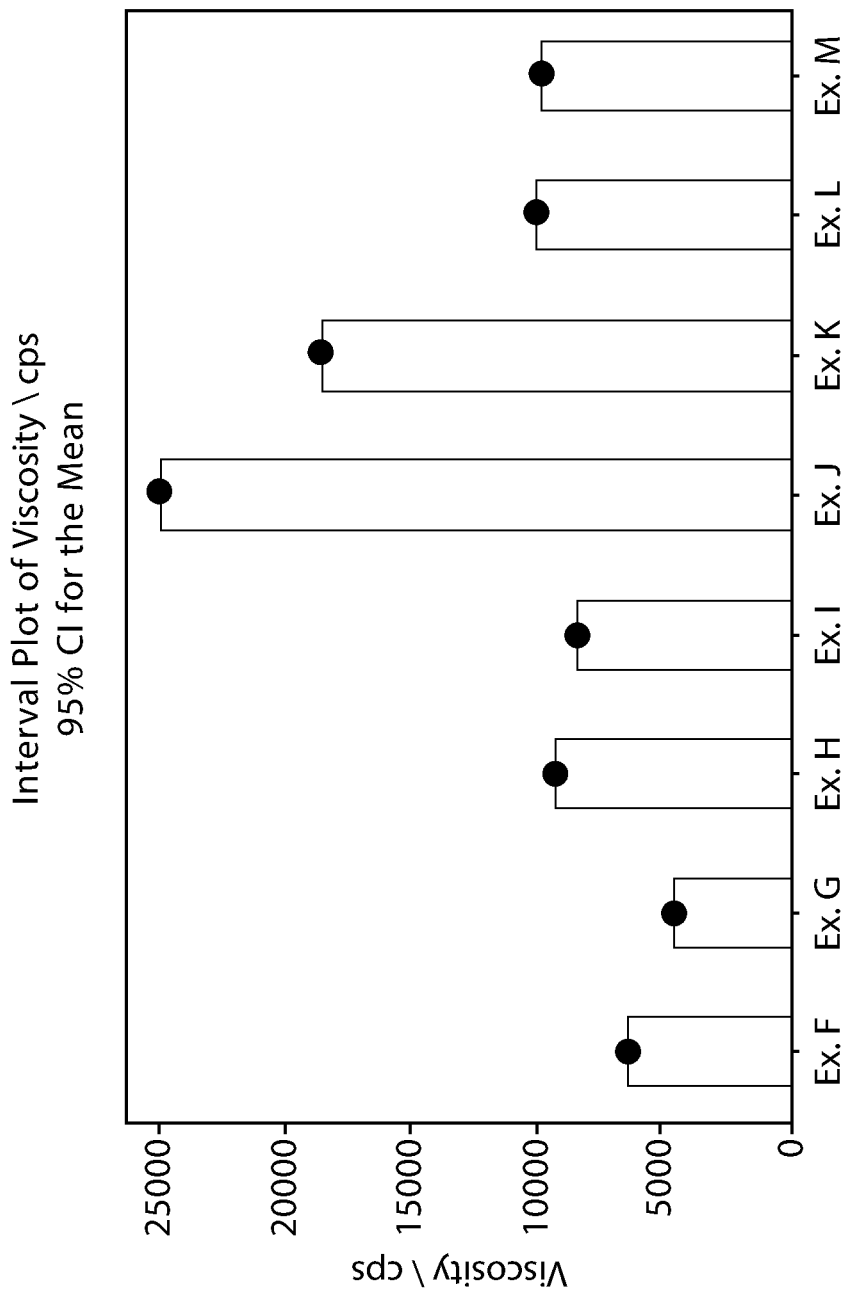
FIG. 3 is a bar graph of the viscosity of hair care compositions in accordance with aspects of the invention.

For evaluating the viscosity of Example Compositions F-M and Comparative Compositions 1, a 300 mL or more sample of each of the compositions was measured at a temperature of at 25° C. using a spindle no. 4 at 10 rpm for 1 min in a Brookfield viscometer (see FIG. 3).

Figure 4:
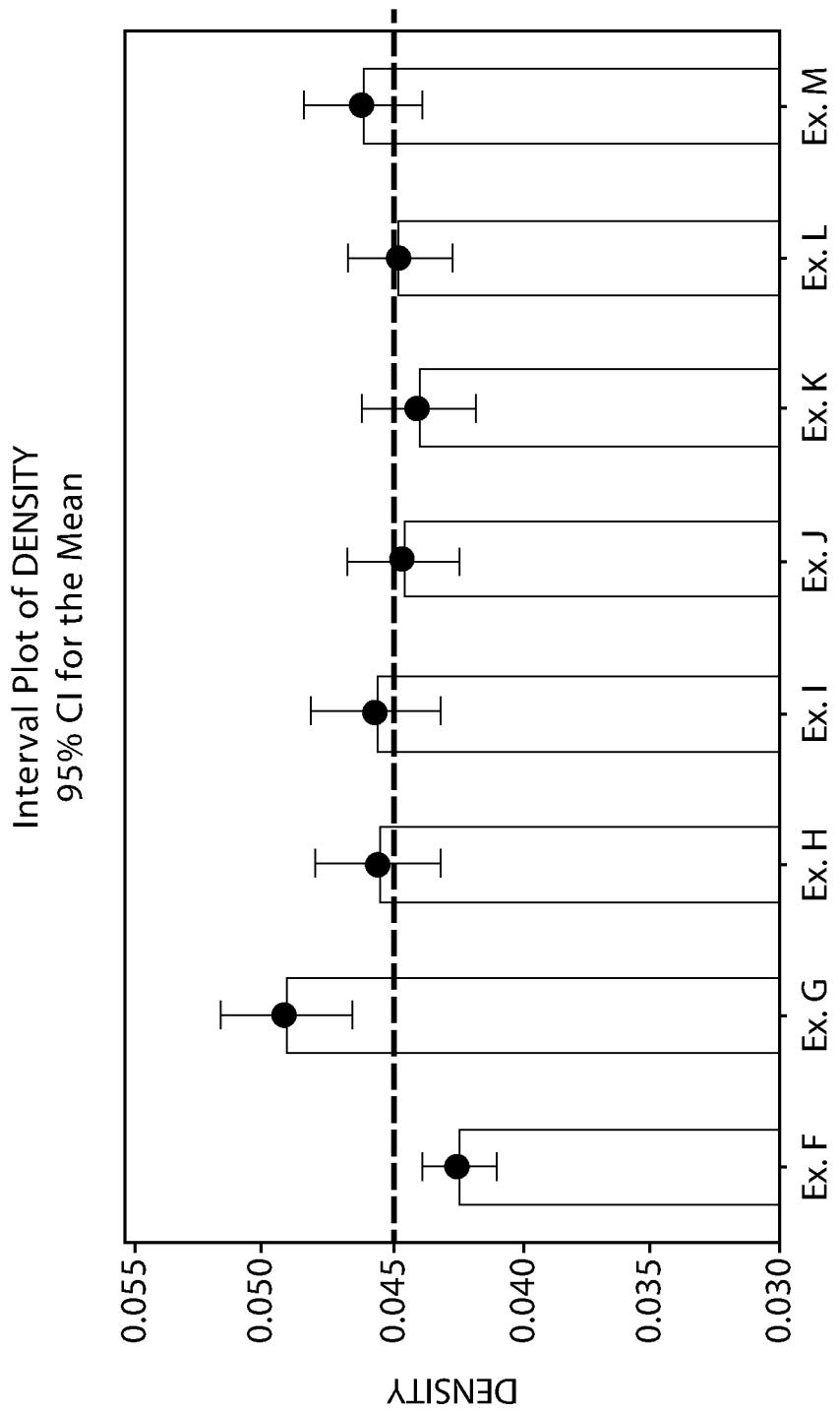
FIG. 4 is a bar graph of the density of hair care compositions in accordance with aspects of the invention.

Foam density was measured by a trained technician using a short hair mannequin head. Specifically, the mannequin's hair was split in two symmetrical sections, with one half of the hair being wetted using 30 mL of running tap water at room temperature. A 1 mL sample of each composition was then applied to both halves of the mannequin's hair and massaged through the hair by hand using circular movements corresponding to a metronome (calibrated at 100 beats per minute). The foam formed was then collected in a beaker of known volumetric capacity and weight. The foam density was then calculated using the determined volume and weight. (see FIG. 4).

Figure 5:
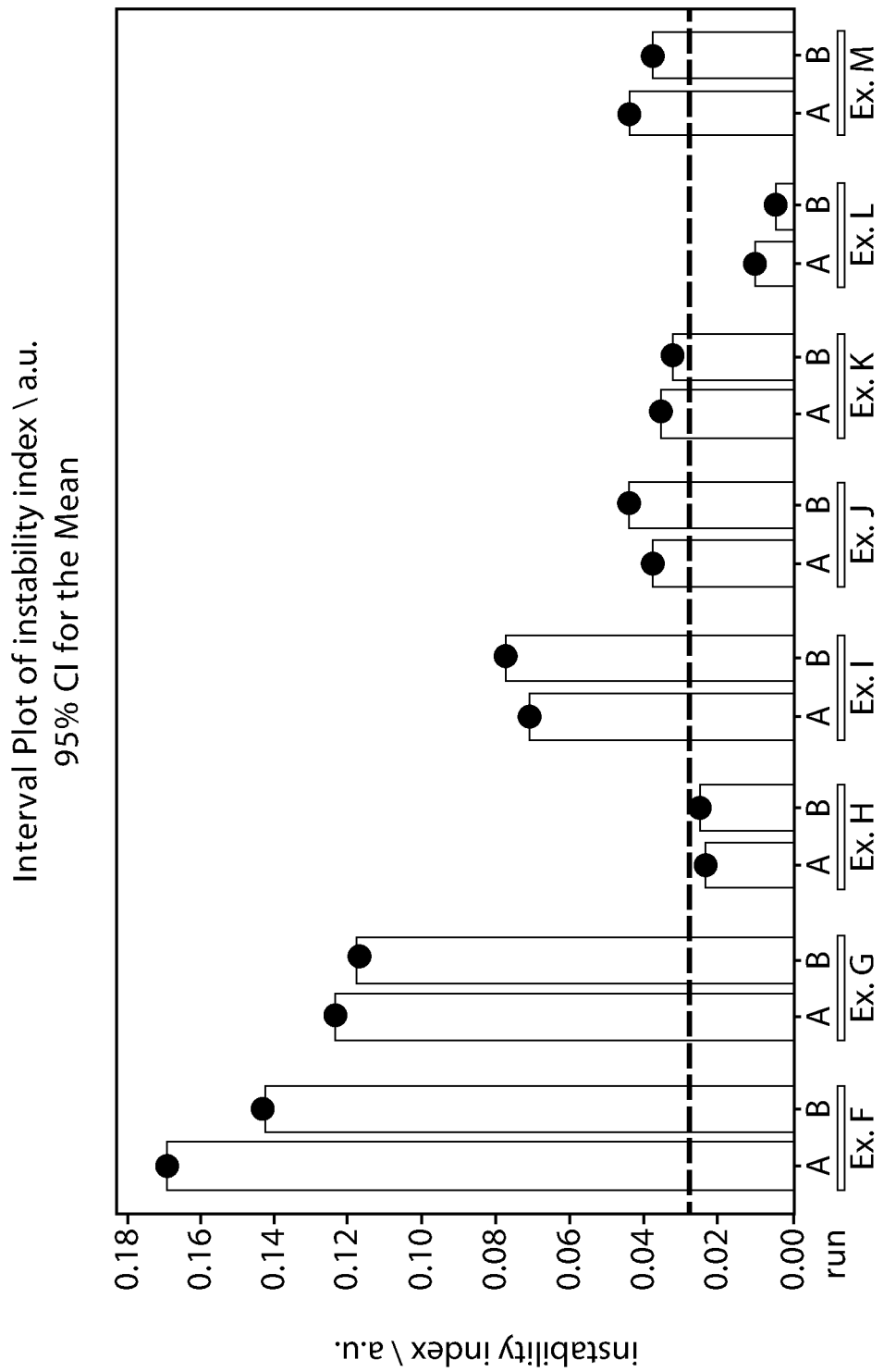
FIG. 5 is a bar graph of the instability of hair care compositions in accordance with aspects of the invention.

To assess the instability of Example Compositions F-M and Comparative Composition 1, samples of each composition were measured using an analytical centrifuge Lumisizer. The instability of the composition, as a parameter, is defined by the equipment supplier and is a measurement of the light transmittance across the sample at different times while the compositions are centrifuged (see FIG. 5).

Figure 6A:
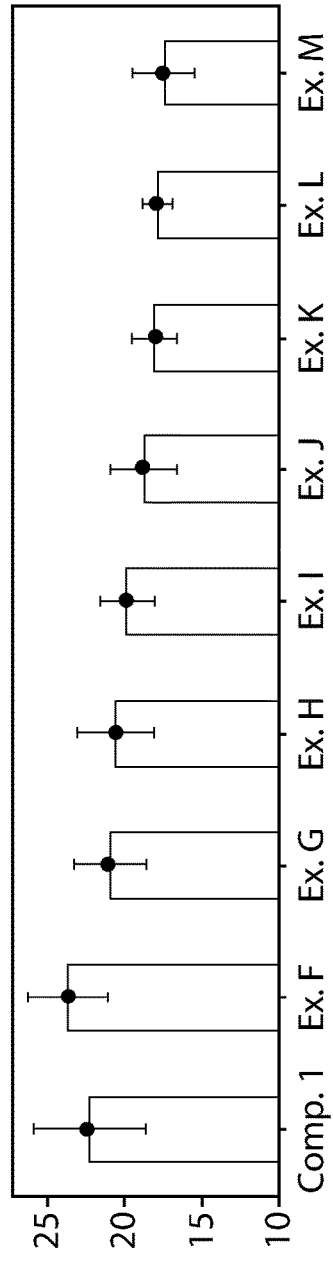
FIGS. 6A and 6B are bar graphs of the detangling force and combing work force of hair after application of a comparative composition and hair care compositions in accordance with aspects of the invention.
Figure 6B:
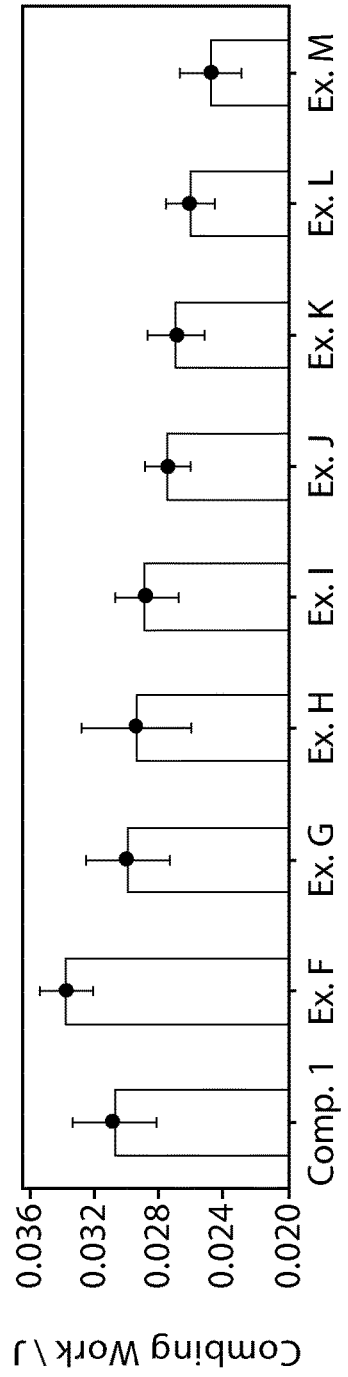

The detangling and combing force provided by Example Compositions F-M and Comparative Composition 1 was assessed using a DIA-STRON Mini-Tensile tester and standardized hair swatches (by hair type, length and weight). A sample of each composition was applied and massaged through the hair swatches. The hair swatches were then rinsed off and measured with the DIA-STRON Mini-Tensile tester (see FIGS. 6A and 6B).

What is claimed is:

1. A hair care composition comprising:
   from about 1 to about 20 wt. % of an anionic surfactant;
   from about 0.1 to about 7 wt. % of an amphoteric surfactant,
   wherein the weight ratio of a total amount of the anionic surfactant to the total amount of amphoteric surfactant is about 5:1 to about 20:1;
   from about 0.1 to about 7 wt. % of a nonionic surfactant;
   from about 0.1 to about 5 wt. % of a thickening agent; and
   from about 0.05 to about 4.5 wt. % of a silicone,
   wherein the nonionic surfactant includes from about 0.3 to about 0.5 wt. % of brassica amido propyl dimethyl amine and/or wherein the hair care composition includes a combination of isoamyl laurate and PPG-3 caprylyl ether, and
   wherein the hair care composition is an emulsion and all weight percentages are based on the total weight of the hair care composition.

2. The hair care composition of claim 1, wherein the anionic surfactant comprises sodium lauryl ether sulfate having an average ethoxylation of about 1 mole per mole of lauryl ether sulfate group.

3. The hair care composition of claim 1, wherein the amphoteric surfactant comprises a betaine surfactant selected from cocamidopropyl betaine, lauryl dimethyl betaine, cetyl dimethyl betaine, and cocoamphodiacetate, and a combination of two or more thereof.

4. The hair care composition of claim 1, wherein the nonionic surfactant is selected from an alkanolamide, a glucoside, a fatty amine, a polyether, and a combination of two more thereof.

5. The hair care composition of claim 4, wherein the glucoside is selected from arachidyl glucoside, $C_{12-20}$ alkyl glucoside, caprylyl/capryl glucoside, cetearyl glucoside, coco-glucoside, lauryl glucoside, decyl glucoside, and a combination of two more thereof.

6. The hair care composition of claim 1, wherein the nonionic surfactant further comprises decyl glucoside, PEG-120 methyl glucose dioleate, coco monoethanolamide, and a combination of two more thereof.

7. The hair care composition of claim 1, further comprising from about 1 to about 10 wt. % of a fatty ester, the fatty ester is selected from isoamyl caprylate, isoamyl caprinate, isoamyl caprate, isoamyl laurate, isoamyl myristate, isoamyl palmitate, isoamyl stearate, isoamyl oleate, isoamyl linolate, isoamyl linoleate, isoamyl behenate, ethylhexyl stearate, hexadecyl stearate, hexyl laurate, isoamyl laurate, PEG-120 jojoba, and a combination of two more thereof.

8. The hair care composition of claim 1, wherein the fatty ester comprises PEG-120 jojoba.

9. The hair care composition of claim 8, wherein the hair care composition has a weight ratio of brassica amido propyl dimethyl amine to PEG-120 Jojoba of from about 1:10 to about 10:1.

10. The hair care composition of claim 8 further comprising a fatty ether, the fatty ether comprising PPG-5-ceteth-10 phosphate, oleth-3 phosphate, oleth-10 phosphate, dicetyl phosphate, PPG-3 caprylyl ether, or a combination of two or more thereof.

11. The hair care composition of claim 1, wherein the hair care composition has a weight ratio of isoamyl laurate to PPG-3 caprylyl ether of from about 1:2 to about 2:1, optionally about 1.14:1.

12. The hair care composition of claim 1, wherein the hair care composition has a weight ratio of isoamyl laurate to PPG-3 caprylyl ether of from about 1:10 to about 10:1, optionally from about 1:7 to about 7:1.

13. The hair care composition of claim 1, wherein the thickening agent comprises hydroxypropyl guar gum, xanthan gum, sclerotium gum, cationic guar, hydroxypropyl guar hydroxypropyltrimonium chloride, or a combination of two more thereof.

14. The hair care composition of claim 1 further comprising from about 0.01 to about 5 wt. % of a cationic polymer, wherein the cationic polymer comprises a monomer selected from dialkyl amincalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, pyridinium, imidazolium, quaternized pyrrolidine, and a combination of two or more thereof.

15. The hair care composition of claim 1 further comprising a cationic surfactant that is selected from behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride, distearyldimonium chloride, dodecyl dimethyl ethylbenzyl ammonium chloride, Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and a combination of two or more thereof.

16. The hair care composition of claim 1 further comprising from about 0.01 to about 10 wt. % of an oil, wherein the oil is a natural oil of plant origin.

17. A hair care composition comprising:
from about 1 to about 20 wt. % of an anionic surfactant;
from about 0.1 to about 7 wt. % of a betaine surfactant,
wherein the weight ratio of the anionic surfactant to the betaine surfactant is about 5:1 to about 20:1;
from about 0.1 to about 7 wt. % of nonionic surfactants;
from about 0.1 to about 10 wt. % of one or more fatty ester comprising PEG-120 jojoba,
from about 0.05 to about 4.5 wt. % of silicone,
wherein the nonionic surfactant includes from about 0.3 to about 0.5 wt. % of brassica amido propyl dimethyl amine and/or wherein the hair care composition includes a combination of isoamyl laurate and PPG-3 caprylyl ether; and
wherein all weight percentages are based on the total weight of the hair care composition.

18. A hair care composition comprising:
from about 1 to about 20 wt. % of an anionic surfactant;
from about 0.1 to about 7 wt. % of a betaine surfactant,
wherein the weight ratio of the anionic surfactant to the betaine surfactant is about 5:1 to about 20:1;
from about 0.1 to about 10 wt. % of one or more fatty ester comprising isoamyl laurate;
from about 0.1 to about 10 wt. % of one or more fatty ether comprising PPG-3 caprylyl ether,
wherein the weight ratio of isoamyl laurate to PPG-3 caprylyl ether is from about 1:10 to about 10:1;
from about 0.05 to about 4.5 wt. % of silicone, and
from about 0.3 to about 0.5 wt. % of brassica amido propyl dimethyl amine;
wherein all weight percentages are based on the total weight of the hair care composition.

19. The hair care composition of claim 18, wherein the silicone comprises dimethiconol.

* * * * *